United States Patent
Noureldin et al.

(10) Patent No.: US 10,801,785 B2
(45) Date of Patent: *Oct. 13, 2020

(54) RECOVERY AND RE-USE OF WASTE ENERGY IN INDUSTRIAL FACILITIES

(71) Applicant: Saudi Arabian Oil Company, Dhahran (SA)

(72) Inventors: Mahmoud Bahy Mahmoud Noureldin, Dhahran (SA); Hani Mohammed Al Saed, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/180,921

(22) Filed: Nov. 5, 2018

(65) Prior Publication Data

US 2019/0072337 A1    Mar. 7, 2019

Related U.S. Application Data

(63) Continuation of application No. 15/241,942, filed on Aug. 19, 2016, now Pat. No. 10,126,067.
(Continued)

(51) Int. Cl.
   *F28D 7/00*       (2006.01)
   *C10G 45/02*     (2006.01)
   (Continued)

(52) U.S. Cl.
   CPC ........... *F28D 7/0083* (2013.01); *B01D 3/007* (2013.01); *B01D 3/32* (2013.01); *B01D 51/10* (2013.01);
   (Continued)

(58) Field of Classification Search
   CPC .............. B01D 53/047; B01D 53/1462; B01D 53/183; B01D 53/343; B01D 53/48;
   (Continued)

(56) References Cited

U.S. PATENT DOCUMENTS 3,995,428 A   12/1976   Roberts
4,109,469 A    8/1978   Carson
(Continued)

FOREIGN PATENT DOCUMENTS

CN            1844325       10/2006
CN          101389736        3/2009
(Continued)

OTHER PUBLICATIONS

D. Ayou, J. C. Bruno, R. Saravanan and A. Coronas, "An Overview of Combined Absorption Power and Cooling Cycles," Renewable sustainable energy reviews, 21 (2013), 728-748.
(Continued)

*Primary Examiner* — Brian A McCaig
(74) *Attorney, Agent, or Firm* — Fish & Richardson P.C.

(57) ABSTRACT

Configurations and related processing schemes of direct or indirect inter-plants heating systems (or both) synthesized for grassroots medium grade crude oil semi-conversion refineries to increase energy efficiency from specific portions of low grade waste heat sources are described. Configurations and related processing schemes of direct or indirect inter-plants heating systems (or both) synthesized for integrated medium grade crude oil semi-conversion refineries and aromatics complex for increasing energy efficiency from specific portions of low grade waste sources are also described.

40 Claims, 26 Drawing Sheets

Related U.S. Application Data

(60) Provisional application No. 62/209,217, filed on Aug. 24, 2015, provisional application No. 62/209,147, filed on Aug. 24, 2015, provisional application No. 62/209,188, filed on Aug. 24, 2015, provisional application No. 62/209,223, filed on Aug. 24, 2015.

(51) Int. Cl.

| | | |
|---|---|---|
| *C10G 35/04* | (2006.01) | |
| *C10L 3/10* | (2006.01) | |
| *C07C 7/08* | (2006.01) | |
| *C10G 65/12* | (2006.01) | |
| *C10G 33/06* | (2006.01) | |
| *C10G 45/00* | (2006.01) | |
| *C10K 3/04* | (2006.01) | |
| *F01K 27/00* | (2006.01) | |
| *C01B 3/34* | (2006.01) | |
| *B01D 3/00* | (2006.01) | |
| *B01D 3/32* | (2006.01) | |
| *B01D 51/10* | (2006.01) | |
| *B01D 53/047* | (2006.01) | |
| *B01D 53/14* | (2006.01) | |
| *B01D 53/18* | (2006.01) | |
| *B01D 53/34* | (2006.01) | |
| *B01D 53/48* | (2006.01) | |
| *B01D 53/86* | (2006.01) | |
| *B01D 53/96* | (2006.01) | |
| *C02F 1/58* | (2006.01) | |
| *C10G 45/44* | (2006.01) | |
| *C10G 47/00* | (2006.01) | |
| *F28F 9/26* | (2006.01) | |
| *C10G 65/00* | (2006.01) | |
| *F01D 17/14* | (2006.01) | |
| *F01K 3/18* | (2006.01) | |
| *F01K 13/02* | (2006.01) | |
| *H02K 7/18* | (2006.01) | |
| *C10G 69/00* | (2006.01) | |
| *F01K 25/06* | (2006.01) | |
| *F01K 25/08* | (2006.01) | |
| *F01K 27/02* | (2006.01) | |
| *F01K 13/00* | (2006.01) | |
| *F01K 23/06* | (2006.01) | |
| *C01B 3/24* | (2006.01) | |
| *C02F 101/10* | (2006.01) | |
| *C02F 101/16* | (2006.01) | |
| *C02F 103/18* | (2006.01) | |
| *C02F 103/36* | (2006.01) | |

(52) U.S. Cl.
CPC ....... *B01D 53/047* (2013.01); *B01D 53/1462* (2013.01); *B01D 53/185* (2013.01); *B01D 53/343* (2013.01); *B01D 53/48* (2013.01); *B01D 53/8603* (2013.01); *B01D 53/96* (2013.01); *C01B 3/24* (2013.01); *C01B 3/34* (2013.01); *C02F 1/586* (2013.01); *C07C 7/08* (2013.01); *C10G 33/06* (2013.01); *C10G 35/04* (2013.01); *C10G 45/00* (2013.01); *C10G 45/02* (2013.01); *C10G 45/44* (2013.01); *C10G 47/00* (2013.01); *C10G 65/00* (2013.01); *C10G 65/12* (2013.01); *C10G 69/00* (2013.01); *C10K 3/04* (2013.01); *C10L 3/101* (2013.01); *C10L 3/103* (2013.01); *C10L 3/104* (2013.01); *F01D 17/145* (2013.01); *F01K 3/185* (2013.01); *F01K 13/00* (2013.01); *F01K 13/02* (2013.01); *F01K 23/06* (2013.01); *F01K 23/064* (2013.01); *F01K 25/06* (2013.01); *F01K 25/08* (2013.01); *F01K 27/00* (2013.01); *F01K 27/02* (2013.01); *F28F 9/26* (2013.01); *H02K 7/1823* (2013.01); *B01D 2252/204* (2013.01); *C01B 2203/0227* (2013.01); *C01B 2203/0233* (2013.01); *C01B 2203/0283* (2013.01); *C01B 2203/043* (2013.01); *C01B 2203/127* (2013.01); *C02F 2101/10* (2013.01); *C02F 2101/101* (2013.01); *C02F 2101/16* (2013.01); *C02F 2103/18* (2013.01); *C02F 2103/36* (2013.01); *C10G 2300/202* (2013.01); *C10G 2300/207* (2013.01); *C10G 2300/4006* (2013.01); *C10G 2300/4056* (2013.01); *C10G 2400/04* (2013.01); *C10G 2400/30* (2013.01); *C10L 2290/06* (2013.01); *C10L 2290/541* (2013.01); *Y02P 20/129* (2015.11); *Y02P 30/10* (2015.11)

(58) Field of Classification Search
CPC .... B01D 53/8603; B01D 53/96; B01D 51/10; B01D 3/007; B01D 3/32; F28D 7/0083; F01K 27/00; C01B 3/34; C10G 45/00; C10G 45/44; C10G 47/00; C10K 3/04; C02F 1/586; F28F 9/26
See application file for complete search history.

(56) References Cited

U.S. PATENT DOCUMENTS

| | | |
|---|---|---|
| 4,291,232 A | 9/1981 | Cardone |
| 4,471,619 A | 9/1984 | Nolley, Jr. |
| 4,512,155 A | 4/1985 | Sheinbaum |
| 4,792,390 A | 12/1988 | Staggs |
| 4,962,238 A | 10/1990 | Wolfe |
| 5,007,240 A | 4/1991 | Ishida |
| 5,164,070 A | 11/1992 | Munro |
| 5,240,476 A | 8/1993 | Hegarty |
| 5,497,624 A | 3/1996 | Amir |
| 6,733,636 B1 | 5/2004 | Heins |
| 8,046,999 B2 | 11/2011 | Doty |
| 9,328,634 B2 | 5/2016 | Ikegami |
| 9,562,201 B2 | 2/2017 | Noureldin |
| 9,851,153 B2 | 12/2017 | Noureldin |
| 2002/0023538 A1 | 2/2002 | Agarwal |
| 2003/0092952 A1 | 5/2003 | Netzer |
| 2003/0132138 A1 | 7/2003 | Mehra |
| 2004/0088993 A1 | 5/2004 | Radcliff et al. |
| 2004/0186332 A1 | 9/2004 | Kong |
| 2006/0010872 A1 | 1/2006 | Singh |
| 2008/0128134 A1 | 6/2008 | Mudunuri |
| 2008/0174115 A1 | 7/2008 | Lambirth |
| 2008/0257413 A1 | 10/2008 | Noureldin et al. |
| 2008/0289588 A1 | 11/2008 | Wees et al. |
| 2008/0314726 A1 | 12/2008 | Choros |
| 2009/0000299 A1 | 1/2009 | Ast |
| 2009/0000906 A1 | 1/2009 | Petri |
| 2009/0071652 A1 | 3/2009 | Vinegar |
| 2009/0225929 A1 | 9/2009 | Genta et al. |
| 2009/0287029 A1 | 11/2009 | Anumakonda et al. |
| 2009/0301087 A1 | 12/2009 | Borissov et al. |
| 2010/0146974 A1 | 6/2010 | Ast |
| 2010/0242476 A1 | 9/2010 | Ast |
| 2010/0263380 A1 | 10/2010 | Biederman |
| 2010/0319346 A1 | 12/2010 | Ast |
| 2010/0326076 A1 | 12/2010 | Ast |
| 2011/0016863 A1 | 1/2011 | Ernst |
| 2011/0072819 A1 | 3/2011 | Silva |
| 2011/0072820 A1 | 3/2011 | Finkenrath |
| 2011/0083437 A1 | 4/2011 | Ast |
| 2011/0158858 A1 | 6/2011 | Alves |
| 2012/0031096 A1 | 2/2012 | Acikgoz et al. |
| 2012/0047889 A1 | 3/2012 | Acikgoz et al. |
| 2012/0048718 A1 | 3/2012 | Werba |
| 2012/0085096 A1 | 4/2012 | Penton et al. |
| 2012/0131921 A1 | 5/2012 | Held |

(56) References Cited

U.S. PATENT DOCUMENTS

| | | |
|---|---|---|
| 2012/0273204 A1 | 11/2012 | De Francesco |
| 2012/0279728 A1 | 11/2012 | Northrop |
| 2012/0279900 A1 | 11/2012 | Noureldin et al. |
| 2012/0285169 A1 | 11/2012 | Freund |
| 2012/0298552 A1 | 11/2012 | Koseoglu |
| 2013/0104546 A1 | 5/2013 | Goswami |
| 2013/0145763 A1 | 6/2013 | Mirmobin et al. |
| 2013/0165534 A1 | 6/2013 | McComish |
| 2013/0213040 A1 | 8/2013 | Goswami |
| 2013/0231909 A1 | 9/2013 | Noureldin |
| 2013/0238154 A1 | 9/2013 | Noureldin |
| 2013/0334060 A1 | 12/2013 | Koseoglu et al. |
| 2014/0090405 A1 | 4/2014 | Held et al. |
| 2014/0142364 A1 | 5/2014 | Io |
| 2014/0260311 A1 | 9/2014 | Berlowitz |
| 2015/0050741 A1 | 2/2015 | Tour et al. |
| 2015/0159079 A1 | 6/2015 | Huh et al. |
| 2015/0252692 A1 | 9/2015 | Honkatukia et al. |
| 2015/0377079 A1 | 12/2015 | Noureldin |
| 2016/0045841 A1 | 2/2016 | Kaplan |
| 2017/0058206 A1 | 3/2017 | Noureldin et al. |
| 2017/0082373 A1 | 3/2017 | Noureldin et al. |

FOREIGN PATENT DOCUMENTS

| | | |
|---|---|---|
| CN | 101424453 | 5/2009 |
| CN | 102027096 | 4/2011 |
| CN | 102371108 | 3/2012 |
| CN | 102796558 | 11/2012 |
| CN | 102947423 | 2/2013 |
| CN | 103170215 | 6/2013 |
| CN | 203928084 | 11/2014 |
| CN | 104560082 | 4/2015 |
| CN | 104619959 | 5/2015 |
| CN | 107364424 | 11/2017 |
| DE | 3731978 | 3/1988 |
| EP | 292391 | 11/1988 |
| EP | 949318 | 10/1999 |
| EP | 2516326 | 10/2012 |
| FR | 2990990 | 11/2013 |
| JP | 2000080905 | 3/2000 |
| SU | 295317 | 10/1977 |
| WO | 97/21786 | 6/1997 |
| WO | 2004102082 | 11/2004 |
| WO | 2011090553 | 7/2011 |
| WO | 2012048132 | 4/2012 |
| WO | 2012158478 | 11/2012 |
| WO | 2013055864 | 4/2013 |
| WO | 2014205163 | 12/2014 |
| WO | WO 2015006872 | 1/2015 |

OTHER PUBLICATIONS

D. Zheng, B. Chen, Y. Qi and H. Jin, "Thermodynamic analysis of a novel absorption power/cooling combined cycle," Applied Energy, 83 (2006), 311-323.

Feng Xu, D. Yogi Goswami and Sunil S. Bhagwat, "A combined power/cooling cycle," Energy, 25 (2000), 233-246.

Gary, "Petroleum Refining Technology and Economics: Figure 1.1 Refinery Flow Diagram," CRC Press, 5th ed., 2007, p. 3.

Hasan et al., "First and Second Law Analysis of a New Power and Refrigeration Thermodynamic Cycle using a Solar Heat Source," Pergamon, Solar Energy, vol. 73, No. 5, Nov. 1, 2002, pp. 385-393.

J. Hua, Y. Chen, Y. Wang and A.P. Roskilly, "Thermodynamic analysis of ammonia-water power/chilling cogeneration cycle with low grade waste heat," Applied thermal engineering, 64 (2014), 483-490.

J. Wang, Y. Dai and L. Gao, "Parametric analysis and optimization for a combined power and refrigeration cycle," Applied Energy, 85 (2008), 1071-1085.

Marcilly, "Acido-Basic Catalysis: Applications to refining and Petrochemistry," IFP Publications, 2005, pp. 512-513.

Meng Liu, and Na Zhang, "Proposal and analysis of a novel ammonia-water cycle for power and refrigeration cogeneration," Energy, 32 (2007), 961-970.

R.V. Padilla, G. Demirkaya, D. Yogi Goswami, E. Stefanakos, and M. A. Rahman, "Analysis of power and cooling cogeneration using ammonia-water mixture," Energy, 35 (2010), 4649-4657.

Sadrameli et al., "Optimum Operating Conditions for a Combined Power and Cooling Thermodynamic Cycle," Science Direct, Applied Energy, vol. 84, No. 3, Nov. 10, 2006, pp. 254-265.

Schaschke, "A Dictionary of Chemical Engineering: Tatoray Process," Oxford, 2014, p. 371.

Stecco, "Kalina Cycles: Some Possible Applications and Comments," Proceedings of the American Power Conference, XP000609703, Jan. 1, 1993, vol. 1, pp. 196-201.

Tamm et al., "Theoretical and Experimental Investigation of an Ammonia-Water Power and Refrigeration Thermodynamic Cycle," Science Direct, Solar Energy, vol. 76, No. 1-3, Jan. 1, 2004, pp. 217-228.

Vidal, "Analysis of a Combined Power and Refrigeration Cycle by the Exergy Method," Science Direct, Energy 31, Dec. 1, 2006, pp. 3401-3414.

PCT International Search Report and Written Opinion of the International Searching Authority, PCT/US2016/048074, dated Nov. 9, 2016, 12 pages.

PCT International Search Report and Written Opinion of the International Searching Authority, PCT/US2016/048042, dated Nov. 9, 2016, 12 pages.

PCT International Search Report and Written Opinion of the International Searching Authority, PCT/US2016/048067, dated Nov. 15, 2016, 11 pages.

PCT International Search Report and Written Opinion of the International Searching Authority, PCT/US2016/048066, dated Nov. 15, 2016, 11 pages.

PCT International Search Report and Written Opinion of the International Searching Authority, PCT/US2016/048078, dated Nov. 15, 2016, 12 pages.

PCT International Search Report and Written Opinion of the International Searching Authority, PCT/US2016/048076, dated Nov. 15, 2016, 12 pages.

PCT International Search Report and Written Opinion of the International Searching Authority, PCT/US2016/048207, dated Nov. 21, 2016, 12 pages.

PCT International Search Report and Written Opinion of the International Searching Authority, PCT/US2016/048219, dated Nov. 21, 2016, 13 pages.

PCT International Search Report and Written Opinion of the International Searching Authority, PCT/US2016/048229, dated Nov. 21, 2016, 13 pages.

PCT International Search Report and Written Opinion of the International Searching Authority, PCT/US2016/048236, dated Nov. 21, 2016, 13 pages.

PCT International Search Report and Written Opinion of the International Searching Authority, PCT/US2016/027413, dated Nov. 22, 2016, 11 pages.

PCT International Search Report and Written Opinion of the International Searching Authority, PCT/US2016/048063, dated Nov. 23, 2016, 11 pages.

PCT International Search Report and Written Opinion of the International Searching Authority, PCT/US2016/048071, dated Nov. 23, 2016, 11 pages.

PCT International Search Report and Written Opinion of the International Searching Authority, PCT/US2016/048210, dated Dec. 22, 2016, 11 pages.

PCT International Search Report and Written Opinion of the International Searching Authority, PCT/US2016/048224, dated Dec. 22, 2016, 11 pages.

PCT International Search Report and Written Opinion of the International Searching Authority, PCT/US2016/048209, dated Dec. 22, 2016, 11 pages.

PCT International Search Report and Written Opinion of the International Searching Authority, PCT/US2016/048237, dated Dec. 22, 2016, 11 pages.

(56) References Cited

OTHER PUBLICATIONS

PCT International Search Report and Written Opinion of the International Searching Authority, PCT/US2016/048223, dated Dec. 22, 2016, 11 pages.

PCT International Search Report and Written Opinion of the International Searching Authority, PCT/US2016/048212, dated Dec. 22, 2016, 11 pages.

Communication Pursuant to Article 94(3) issued in European Application No. 16758058.8 dated Apr. 18, 2019, 4 pages.

European Office Action in European Application No. 16758061.2-1101, dated Aug. 20, 2019. 6 pages.

Oluleye et al, "Evaluating the potential of process sites for waste heat recovery", Applied Energy., vol. 161, Jul. 23, 2015, pp. 627-646.

Gulf Cooperation Council Examination Report issued in GCC Application No. GC 2016-31904 dated Nov. 13, 2018, 3 pages.

Gulf Cooperation Council Examination Report issued in GCC Application No. GC 2016-31907 dated Nov. 13, 2018, 3 pages.

Gulf Cooperation Council Examination Report issued in GCC Application No. GC 2016-31906 dated Nov. 13, 2018, 3 pages.

Gulf Cooperation Council Examination Report issued in GCC Application No. GC 2016-31908 dated Nov. 13, 2018, 3 pages.

CN Office Action in Chinese Appln. No. 201680061070.5, dated Aug. 27, 2019, 11 pages (with English translation).

CN Office Action in Chinese Appln. No. 201680061004.8, dated Sep. 3, 2019, 16 pages (with English translation).

Communication Pursuant to Article 94(3) EPC issued in European Application No. 16758061.2 dated Dec. 18, 2018, 4 pages.

Chinese Office Action issued in Chinese Application No. 201680060979.9 dated Oct. 28, 2019, 10 pages (with English translation).

Chinese Office Action issued in Chinese Application No. 201680059774.9 dated Oct. 28, 2019, 10 pages (with English translation).

Gulf Cooperation Council Examination Report issued in GCC Application No. GC 2016-31901 dated Nov. 13, 2018, 3 pages.

Gulf Cooperation Council Examination Report issued in GCC Application No. GC 2016-31905 dated Nov. 13, 2018, 3 pages.

Gulf Cooperation Council Examination Report issued in GCC Application No. GC 2016-31902 dated Nov. 13, 2018, 3 pages.

Gulf Cooperation Council Examination Report issued in GCC Application No. GC 2016-31903 dated Nov. 13, 2018, 3 pages.

Gulf Cooperation Council Examination Report issued in GCC Application No. GC 2016-37141 dated Jul. 7, 2019, 3 pages.

Gulf Cooperation Council Examination Report issued in GCC Application No. GC 2016-37123 dated Jul. 7, 2019, 3 pages.

Communication Pursuant to Article 94(3) EPC issued in European Application No. 16758058.8 dated Dec. 11, 2018, 4 pages.

CN Office Action in Chinese Appln. No. 2016800610692, dated Sep. 9 , 2019, 20 pages (with English translation).

Zhang et al, "Total Site Optimization Strategy of Energy System and Application for Petrochemical Industry," Computer and Applied Chemistry, vol. 26, No. 4, pp. 339-402, Apr. 28, 2009, English Abstract 4 pages.

Communication Pursuant to Article 94(3) EPC issued in European Application No. 16758061.2 dated May 28, 2019, 5 pages.

Indian Office Action issued in Indian Application No. 201817009037 dated Mar. 17, 2020, 6 pages.

Communication Pursuant to Article 94(3) EPC issued in European Application No. 16758058.8 dated Dec. 11, 2019, 4 pages.

Communication Pursuant to Article 94(3) EPC issued in European Application No. 16758061.2 dated Dec. 10, 2019, 4 pages.

Chinese Office Action issued in Chinese Application No. 201680061070.5 dated Mar. 12, 2020, 6 pages (with English translation).

Gulf Cooperation Council Examination Report issued in GCC Application No. GC 2016-38077 dated Dec. 16, 2019, 4 pages.

Chinese Office Action issued in Chinese Application No. 201680060979.9 dated May 8, 2020, 6 pages (with English translation).

Chinese Office Action issued in Chinese Application No. 201680059774.9 dated May 8, 2020, 6 pages (with English translation).

Chinese Office Action issued in Chinese Application No. 201680061004.8 dated Apr. 21, 2020, 6 pages (with English translation).

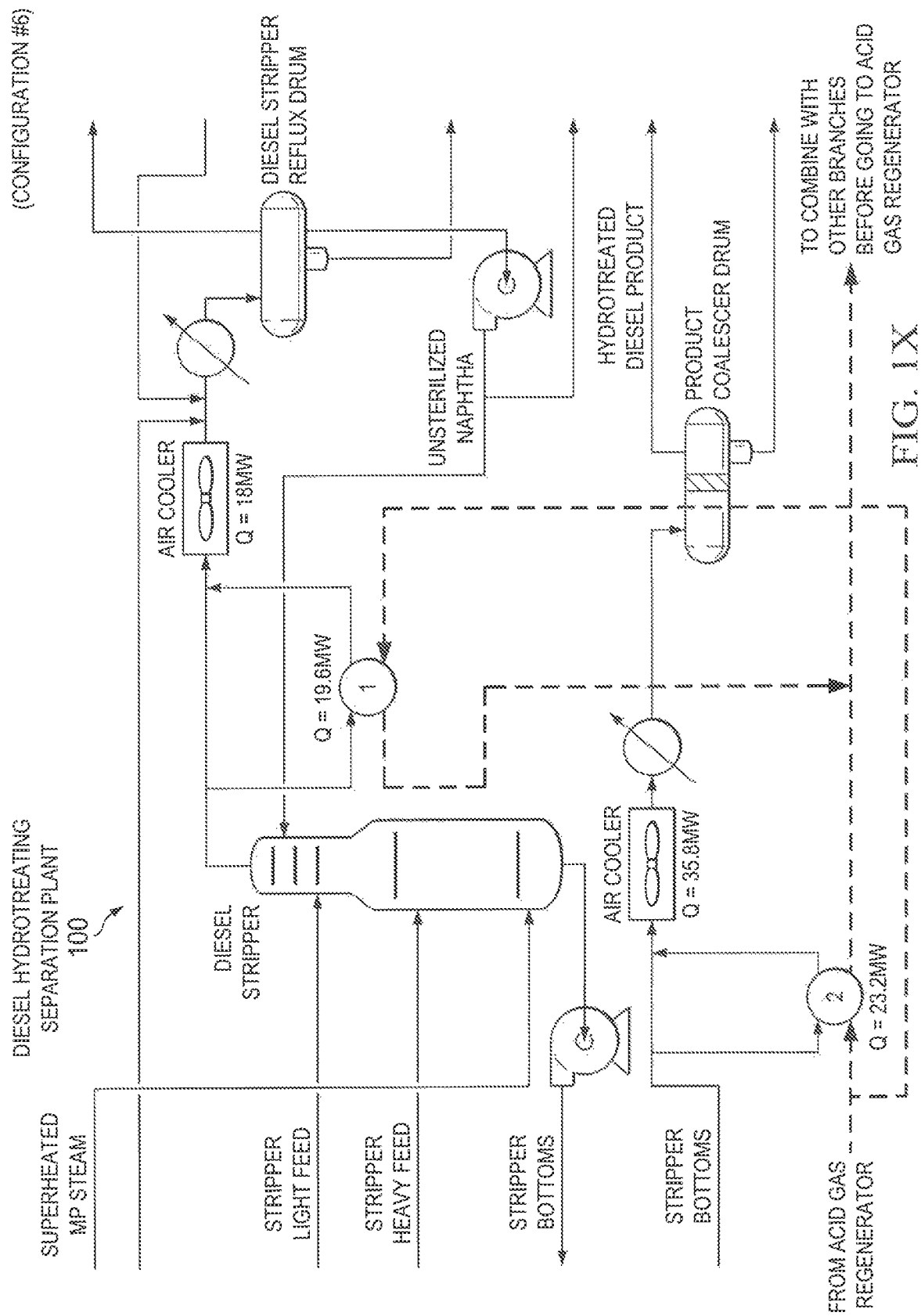
FIG. IX

RECOVERY AND RE-USE OF WASTE ENERGY IN INDUSTRIAL FACILITIES

CROSS-REFERENCE TO RELATED APPLICATIONS

This application is a continuation application of, and claims the benefit of priority under 35 U.S.C. § 120 to U.S. application Ser. No. 15/241,942, filed on Aug. 19, 2016, and also claims priority under 35 U.S.C. § 119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to operating industrial facilities, for example, crude oil refining facilities or other industrial facilities that include operating plants that generate heat.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be reused, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to specific direct or indirect inter-plants and hybrid, intra- and inter-plants integration for energy consumption reduction from waste energy in industrial facilities The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

FIGS. 1M-1O illustrate example schematics of a fourth configuration for indirectly heating an amine regeneration plant stream using a diesel hydro-treating plant stream and a hydrogen plant stream.

FIGS. 1X-1Z illustrate example schematics of a sixth configuration for directly heating an amine regeneration plant stream using a diesel hydro-treating plant stream and a hydrogen plant stream.

DETAILED DESCRIPTION

Figure 1A:
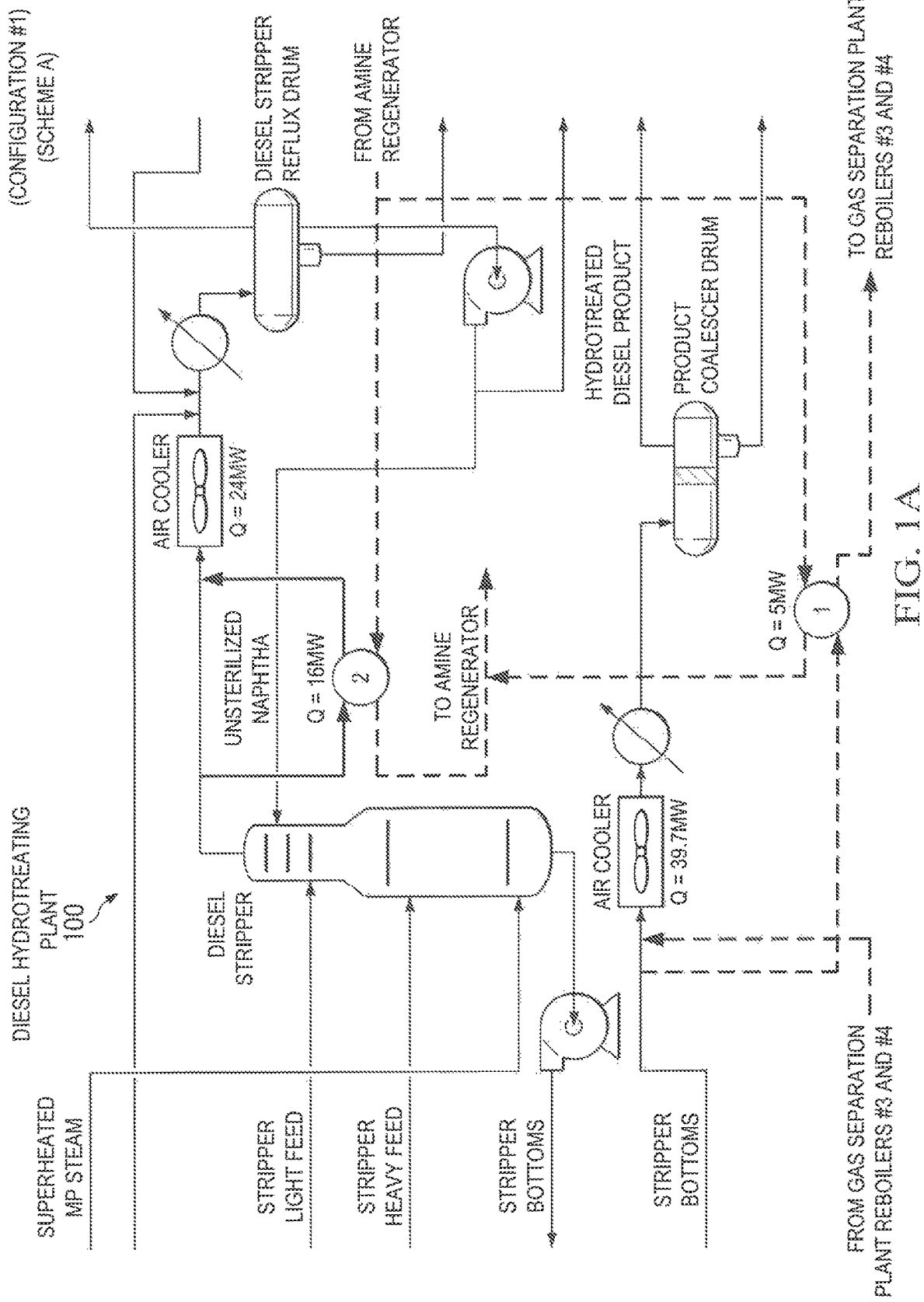
FIGS. 1A-1F illustrate example schematics of a first configuration for heating sulfur recovery plant stream and a gas separation plant stream using a diesel hydro-treating plant stream.

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM Btu/h can be wasted to a network of air coolers extended along the crude oil and aromatics site. Some of the wasted heat can be reused to heat streams in refining sub-units of the crude oil refinery, thereby decreasing a quantity of heat that would otherwise need to be used to heat the streams. In this manner, a quantity of heat consumed by the crude oil refinery can decrease. In addition, a quantity of greenhouse gas (GHG) emission can also decrease. In some implementations, a reduction of about 34% in heating utility consumption and a reduction of about 20% in cooling utility consumption can be achieved without affecting an operational philosophy of the crude oil refinery.

The waste heat recovery and reuse techniques described here can be implemented in medium grade crude oil refining semi-conversion facilities and integrated medium grade crude oil refining semi-conversion oil refining and aromatics facilities. The implementations can result in energy efficient systems that can consume about 66% of the heating utility consumed by current state-of-the-art designs of existing and new crude oil refining facilities. The implementations can also result in decrease in pollution and in GHG emissions by about one-third relative to GHG emissions from current state-of-the-art designs of existing and new crude oil refining facilities.

In certain existing oil refining facilities, a stream in a plant (for example, a naphtha hydro-treating plant, a sour water stripper plant, or other plant) is heated using heat energy generated in a steam reboiler. In some implementations of the subject matter described here, the stream in the plant can be heated using waste heat carried by another stream in another plant (for example, a hydrocracking plant, a hydro-treating plant, a hydrogen plant, or other plant). By doing so, the heat energy generated in the steam reboiler can be decreased or eliminated. In other words, the steam reboiler need not be the only source of heat energy to heat the stream in the plant. The waste heat carried by the other stream in the other plant can either replace the heat energy generated in the steam reboiler or supplement the heat energy thereby decreasing a quantity of heat energy needed from the steam reboiler.

The subject matter described here can be implemented at different plants' specific operating modes and can be retrofitted without the need to change the network designs of existing heat exchanger designs in crude oil refineries. The minimum approach temperature used in the waste heat recovery and reuse processes can be as low as 3° C. In some implementations, higher minimum approach temperatures can be used in an initial phase at the expense of less waste heat/energy recovery, while relatively better energy saving is realized in a subsequent phase upon using the minimum approach temperature for the specific hot sources uses.

In sum, this disclosure describes several crude oil refinery-wide separation/distillation networks, configurations, and processing schemes for increasing energy efficiency of heating/cooling utilities. The increase in energy efficiency is realized by reusing all or part of waste heat, for example, low grade waste heat, carried by multiple, scattered low grade energy quality process streams.

Examples of Crude Oil Refinery Plants

1. Hydrogen Plant

Hydrogen is generally used in refineries for sulfur removal and quality improvement of hydrocarbon products. As sulfur restrictions on gasoline and diesel become stringent, the refining demand for hydrogen continues to grow. Two process schemes are employed in on-purpose hydrogen generation plants—conventional process and pressure swing adsorption (PSA) based process. Hydrogen production can include hydro-desulfurization, steam reforming, shift conversion and purification. The conventional process produces a medium-purity hydrogen, whereas the PSA-based process recovers and purifies the hydrogen to high purities, for example, purities greater than 99.9%.

2. Aromatics Complex

A typical aromatics complex includes a combination of process units for the production of basic petrochemical intermediates of benzene, toluene and xylenes (BTX) using the catalytic reforming of naphtha using continuous catalytic reformer (CCR) technology.

3. Gas Separation Plant

A gas separation plant includes a de-ethanizer and a de-propanizer, which are distillation columns used to isolate ethane and propane, respectively, in natural gas liquids (NGL) and light ends fractionation in gas plants and refineries. The de-ethanizer removes ethane from a mixture of propane, butane and other heavier components. An output of the de-ethanizer is fed to a de-propanizer to separate propane from the mixture.

4. Amine Regeneration Plant

Hydrogen sulfide and carbon dioxide are the most common contaminants present in natural gas and are present in relatively larger quantities than other contaminants which can adversely impact the natural gas processing facility if not removed. Amine is used in an acid gas absorber and regenerator to sweeten sour gases in a chemical process in which a weak base (for example, the amine) reacts with weak acids such as hydrogen sulfide and carbon dioxide to form a weak salt.

5. Hydrocracking Plant

Hydrocracking is a two-stage process combining catalytic cracking and hydrogenation. In this process heavy feedstocks are cracked in the presence of hydrogen to produce more desirable products. The process employs high pressure, high temperature, a catalyst, and hydrogen. Hydrocracking is used for feedstocks that are difficult to process by either catalytic cracking or reforming, since these feedstocks are characterized usually by high polycyclic aromatic content or high concentrations of the two principal catalyst poisons, sulfur and nitrogen compounds (or combinations of them).

The hydrocracking process depends on the nature of the feedstock and the relative rates of the two competing reactions, hydrogenation and cracking. Heavy aromaticsfeedstock is converted into lighter products under a wide range of high pressures and high temperatures in the presence of hydrogen and special catalysts. When the feedstock has a high paraffinic content, hydrogen prevents the formation of polycyclic aromaticscompounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces iso-butane for alkylation feedstock, and also performs isomerization for pour-point control and smoke-point control, both of which are important in high-quality jet fuel.

6. Diesel Hydrotreating Plant

Hydrotreating is a refinery process for reducing sulfur, nitrogen and aromatics while enhancing cetane number, density and smoke point. Hydrotreating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

7. Sour Water Stripper Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

8. Sulfur Recovery Plant

Sulfur recovery facilities in refineries operate to regulate the discharge of sulfur compounds to the atmosphere to meet environmental regulations. In a sulfur recovery plant, combustion products that include sulfur can be processed, for example, by heating, cooling with condensers, using sulfur conversion catalyst, and by other processing techniques. One technique is to use amines to extract the sulfur and other acid gas compounds.

9. Naphtha Hydrotreating Plant and Continuous Catalytic Reformer Plants

A Naphtha Hydrotreater (NHT) produces 101 Research Octane Number (RON) reformate, with a maximum 4.0 psi (pounds per square inch) Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the CCR platformer and gasoline blending.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively less hotter fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-by-side. In cross-flow heat exchangers, the fluid path runs perpendicular to one another. In counter-current heat exchangers, the fluid paths flow in opposite directions, with one fluid exiting whether the other fluid enters. Counter-current heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, that is, the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with threats that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Configurations in which heat exchangers are described as being in series can have multiple implementations. In some implementations, the heat exchangers can be arranged in series in one order (for example, a first heat exchanger, a second heat exchanger and a third heat exchanger in that order) while in other implementations, the heat exchangers can be arranged in series in a different order (for example, a third heat exchanger, a first heat exchanger and a second heat exchanger in that order). In other words, a first heat exchanger described as being in series with and downstream of a second heat exchanger in one implementation can be in series with and upstream of the second heat exchanger in a second, different implementation.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

This specification discloses new energy efficient configurations and the related processing schemes for medium grade semi-conversion crude oil refining facility. A semi-conversion medium grade crude oil refining facility is one that does not include an aromatics complex. This disclosure describes a waste heat recovery and reuse network for such a refining facility. As described later, waste heat can be recovered from one or more of the units in the refining facility. Such a refinery typically consumes several hundred megawatts of energy (for example, about 400 MW) in heating utilities. Implementing the configurations described here can not only reduce energy consumption but also reduce energy-based greenhouse gas (GHG) emissions. In particular, this disclosure describes a method implemented in a crude oil refining facility to heat a stream in a plant of the crude oil refining facility using a diesel hydro-treating plant stream in a diesel hydro-treating plant of the crude oil refining facility. Several configurations of process schemes for doing so are described below with reference to the following figures.

Configuration 1

FIGS. 1A-1F illustrates configurations and related scheme details for heating an amine regenerator stream in a sulfur recovery plant in the crude oil refining facility. The heated sulfur recovery plant stream can further be used to heat an oil refinery gas separation plant stream in an oil refinery gas separation plant of the crude oil refining facility, as described later. The configurations illustrated in FIGS. 1A-1F thermally integrate a diesel hydro-treating plant in a crude oil refining facility with a sulfur recovery plant and a gas separation plant in the crude oil refining facility to reduce thermal energy consumption. For example, a reduction in energy consumption by about 35 MW can translates to about 9% of the heating utility consumption in the crude oil facility. As described later, in certain schemes, a process stream (for example, a sulfur recovery plant stream or other process streams) can be used to directly heat another process stream (for example, a gas separation plant stream or other process stream). In certain configurations, heat exchange between process streams can be implemented using an intermediate buffer fluid, for example, water, oil, or other buffer fluid.

Configuration 1—Scheme A

In some implementations described with reference to FIGS. 1A-1C, streams in the gas separation plant and the sulfur recovery plant can be heated directly using the diesel hydro-treating plant. In some implementations, multiple first streams in multiple first multiple plants can be directly heated using multiple second streams in a second plant. In some implementations, the multiple first plants are the sulfur recovery plant and a gas separation plant; the multiple first streams are the amine regenerator bottoms, the C3/C4 splitter bottoms, and the de-ethanizer bottoms; the second plant is the diesel hydrotreating plant and the second streams are the diesel stripper overheads and the diesel stripper bottoms streams.

FIG. 1A shows a diesel hydro-treating plant 100 in a crude oil refining facility. The amine regenerator bottoms stream can be flowed into the plant as a single stream and split into multiple streams or it can be flowed into the plant as multiple streams. A first and a second amine regenerator bottoms stream from the sulfur recovery plant 102 is flowed to and received at the diesel hydro-treating plant 100. The first amine regenerator bottoms stream is directly heated using a diesel stripper bottom product stream in a first heat exchanger (1, FIG. 1A). The second amine regenerator bottoms stream is directly heated using a diesel stripper overhead stream in a second heat exchanger (2, FIG. 1A). The first and the second heat exchangers are coupled in parallel with one another relative to the flow of amine regenerator bottoms. In some implementations, the thermal duties of the two heat exchangers can range between about 1 MW and 10 MW (for example, 5 MW) and about 11 MW and 21 MW (for example, 16 MW), respectively. The transfer of heat directly to another process stream captures heat that would have otherwise been discharged to the environment. The diesel stripper overhead stream is returned to the diesel hydro-treating plant 100 for further processing.

Figure 1B:
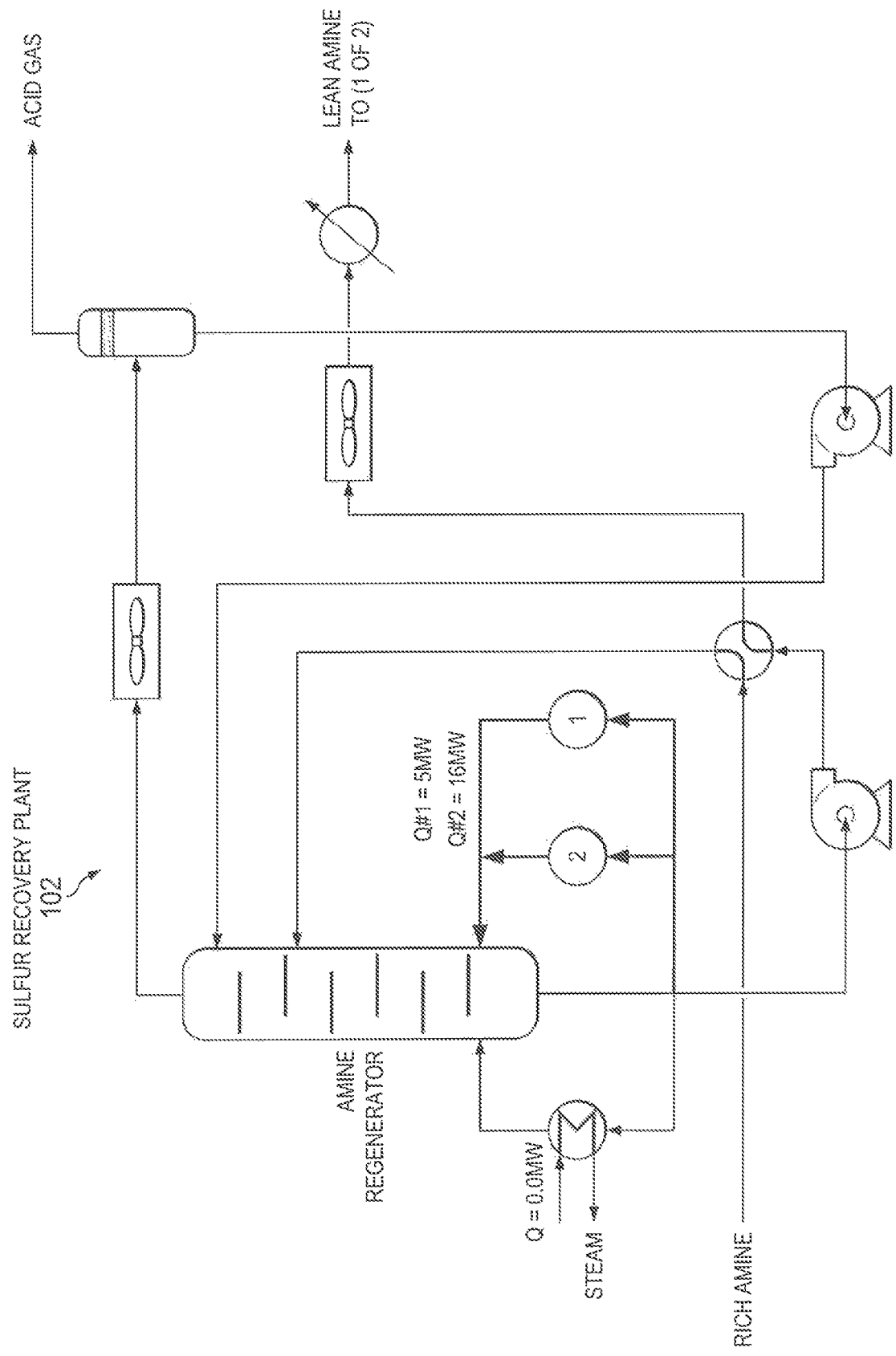

The heated first and second amine regenerator bottoms streams are then combined and flowed to the amine regenerator in the sulfur recovery plant 102 (FIG. 1B). As shown in FIG. 1B, the steam heat input for the amine regenerator can be 0 MW because the alternative flow paths disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

The diesel stripper bottom stream exiting the first heat exchanger is flowed to the gas separation plant 104 third and fourth heat exchangers. The diesel stripper bottoms is split into two portions. For example, a portion of the partially-cooled diesel stripper bottom product stream is used to heat a gas separation plant de-ethanizer stream in a third heat exchanger (3, FIG. 1C) and the remaining portion of the partially-cooled diesel stripper bottom product stream is used to heat a C3/C4 splitter bottom stream in a fourth heat exchanger (4, FIG. 1C). The third and the fourth heat exchangers are coupled in parallel with one another and both as a set are downstream of and in series with the first heat exchanger relative to the flow of the diesel stripper bottom stream. The thermal duties of the third and fourth heat exchangers can range between about 1 MW and 10 MW (for example, 4.3 MW) and 5 MW and 15 MW (for example, 9.9 MW), respectively. As shown in FIG. 1C, the steam heat input for the de-ethanizer column can be 0 MW because the alternative flow paths disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column. Also as shown in FIG. 1C, the steam heat input for the C3/C4 splitter can be 0 MW because the alternative flow paths disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

Figure 1C:
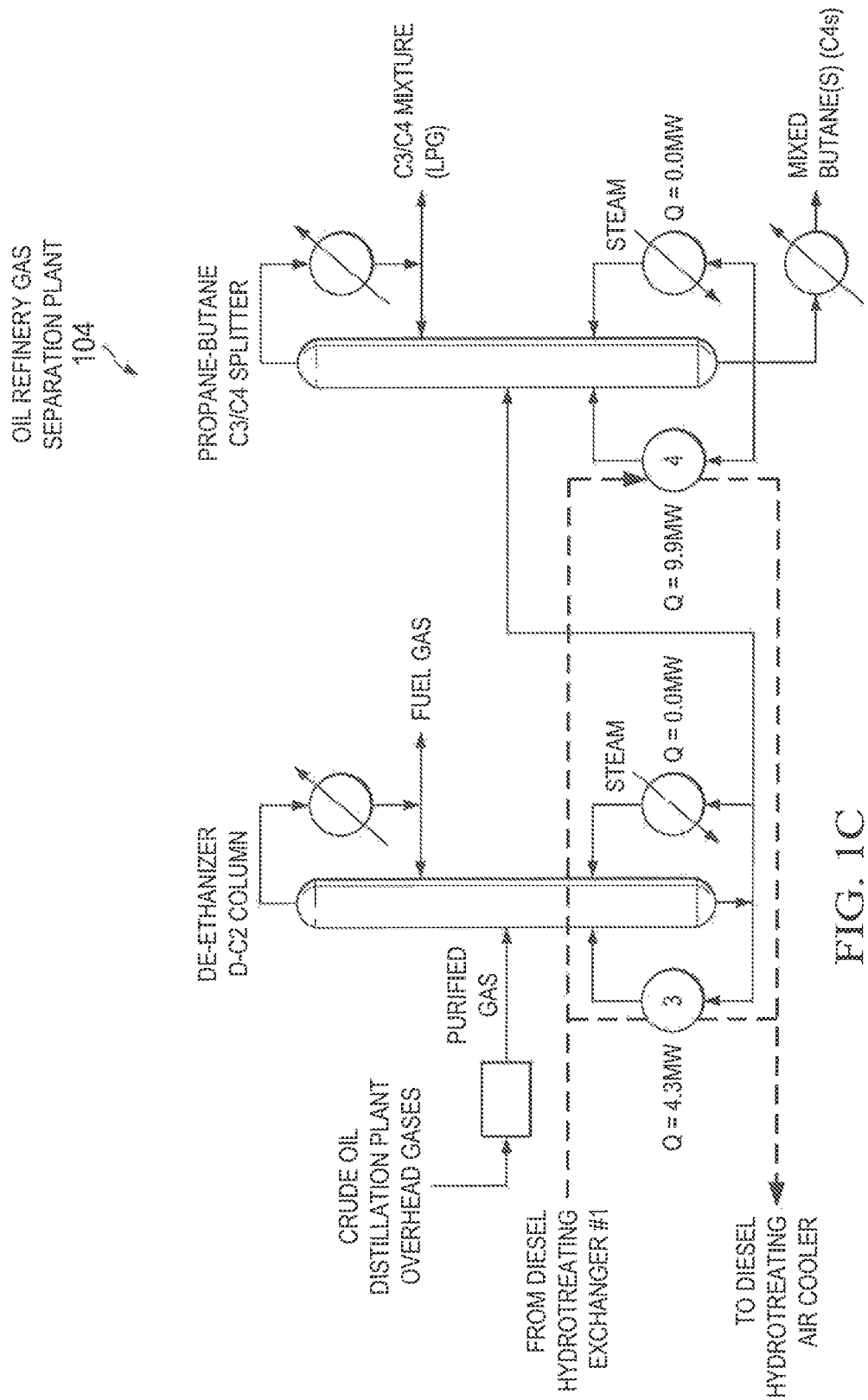

As shown in FIGS. 1A and 1C, the cooled diesel stripper bottom product streams exiting the third and the fourth heat exchangers are recombined and flowed to the diesel hydrotreating plant 100 for further processing.

Such recovery and reuse of waste heat directly from the diesel hydrotreating plant can result in decreasing or eliminating the heat energy to heat the sulfur recovery plant or the gas separation plant or a combination of them such as by about 35 MW.

Configuration 1—Scheme B

In some implementations described with reference to FIGS. 1D-1F, multiple first streams in multiple first plants can be heated indirectly using multiple second streams in a second plant. In some implementations, the multiple first plants include the sulfur recovery plant and a gas separation plant; the multiple first streams are the amine regenerator bottoms, the C3/C4 splitter bottoms, and the de-ethanizer bottoms; the second plant is the diesel hydrotreating plant and the second streams are the diesel stripper overheads and the diesel stripper bottoms streams.

A buffer fluid (for example, high pressure water) from a buffer fluid tank (for example, hot water tank) is flowed to the diesel hydro-treating plant 100. The buffer fluid can be flowed into the plant as a single stream and split into multiple streams or it can be flowed into the plant as multiple streams.

Figure 1D:
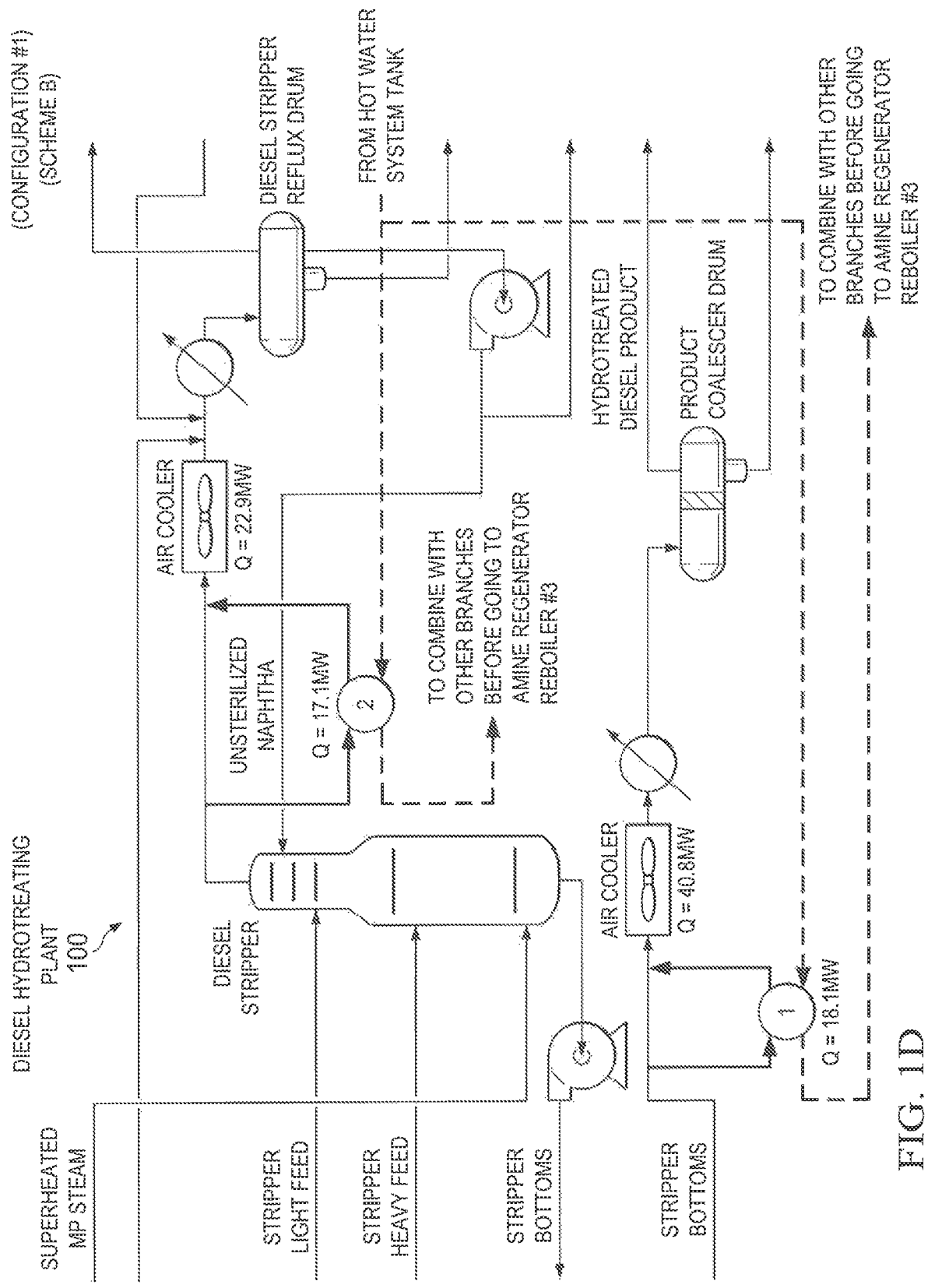
Figure 1E:
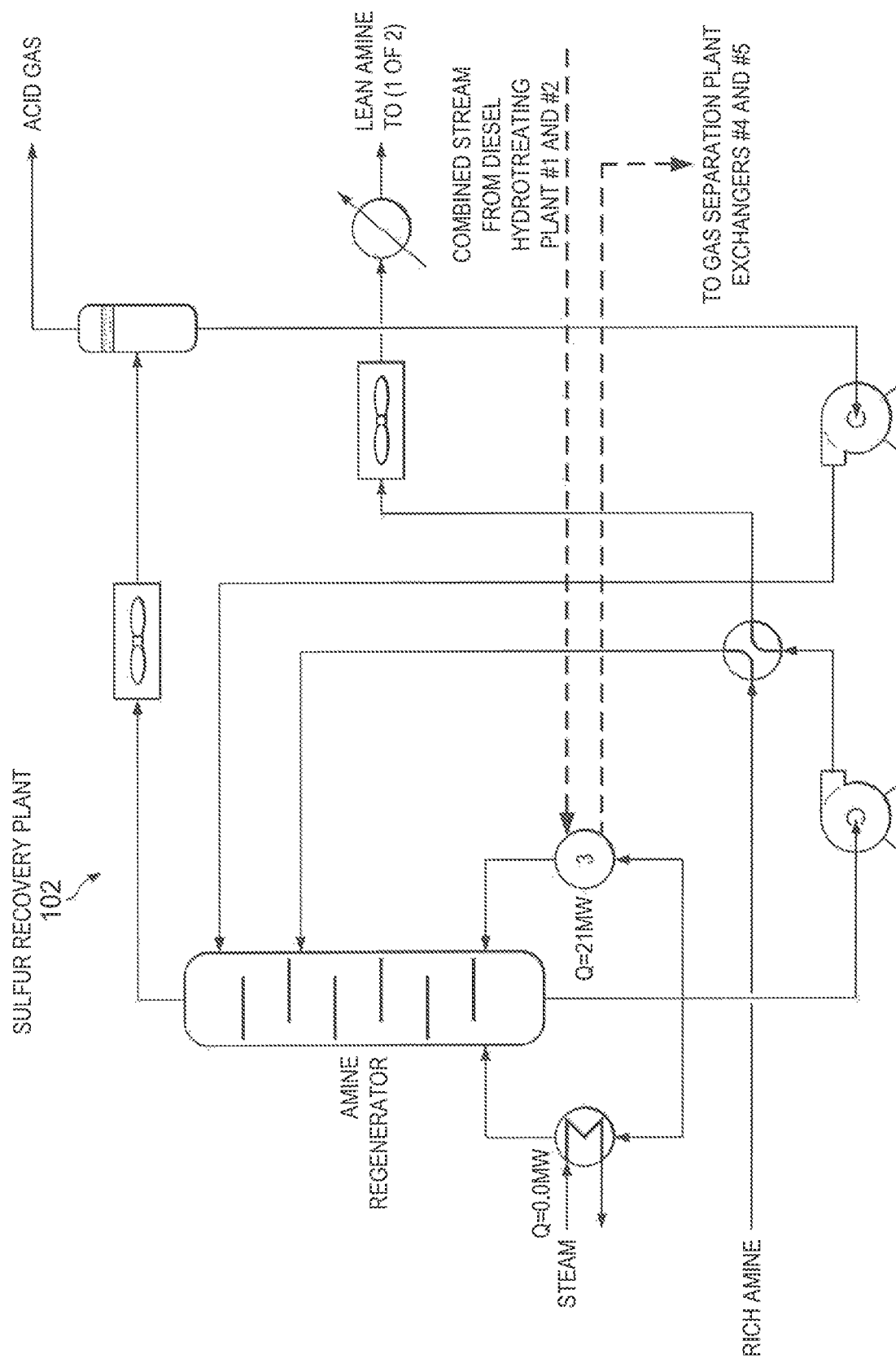
Figure 1F:
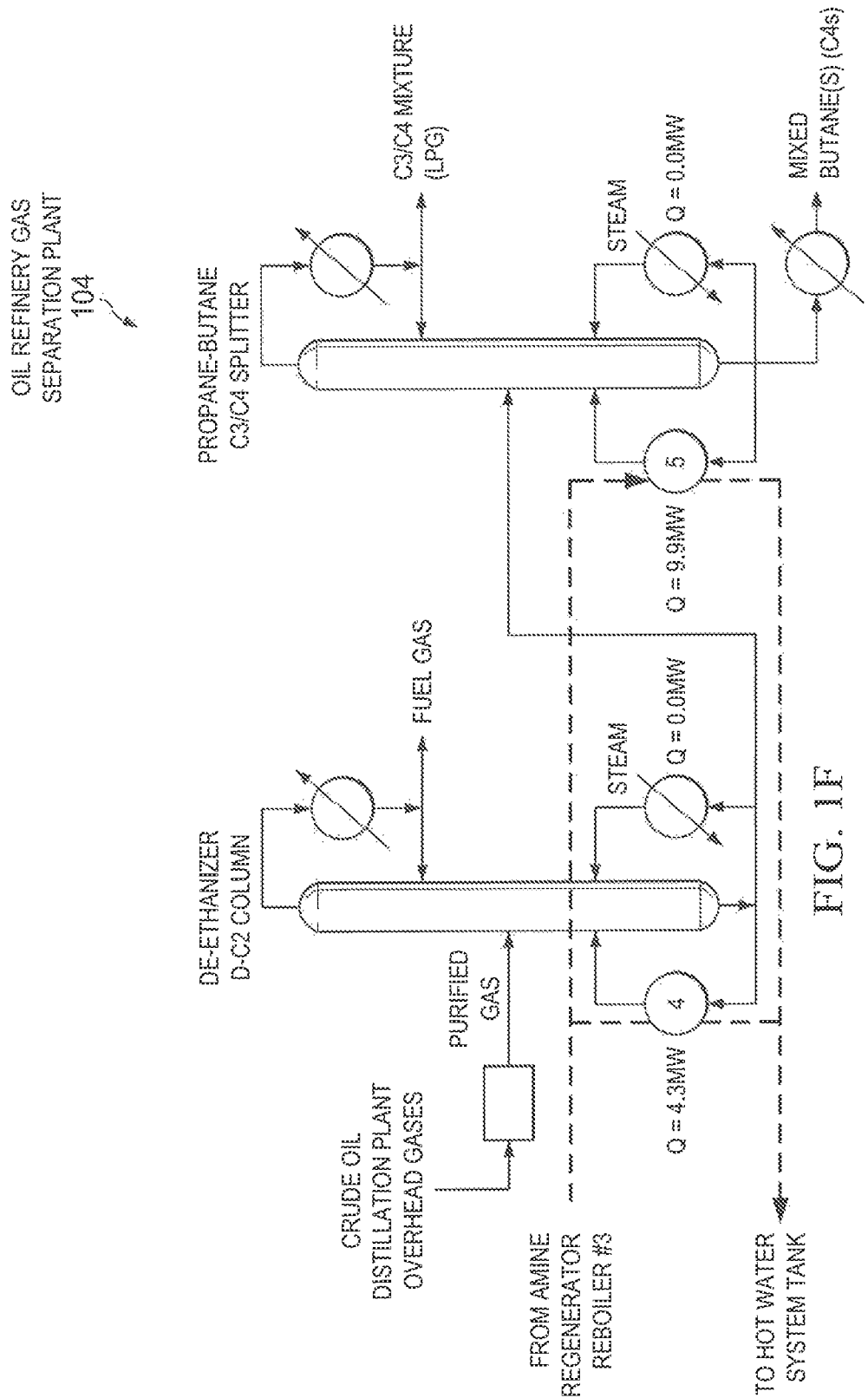

FIG. 1D shows a diesel hydro-treating plant 100 in a crude oil refining facility. The first buffer fluid stream is heated using a diesel stripper bottom product stream in a first heat exchanger (1, FIG. 1D). For example, a thermal duty of the first heat exchanger can range between about 10 MW and 20 MW (for example, 18.1 MW). The second buffer fluid stream is heated using a diesel stripper overhead stream in a second heat exchanger (2, FIG. 1D). For example, the thermal duty of the second heat exchanger can range between about 10 MW and 20 MW (for example, 17.1 MW). The first and the second heat exchangers are coupled in parallel with one another relative to the flow of the buffer fluid. For both of these process streams, the transfer of heat into the buffer fluid captures heat that would have otherwise been discharged to the environment. Both the diesel stripper bottom product stream and the diesel stripper overhead stream are returned to the diesel hydrotreating plant 100 for further processing.

The heated first buffer fluid stream and the heated second buffer fluid stream are combined into a combined heated buffer fluid in a collection header (or in some embodiments, a heated or insulated buffer fluid tank or storage unit that can hold heated collected buffer fluid for a period before use) that can be flowed to a gas separation plant 104 or a sulfur recovery plant 102.

In an embodiment, the buffer fluid is flowed to the sulfur recovery plant 102. FIG. 1E shows the sulfur recovery plant 102 in a crude oil refining facility. An amine regenerator bottom stream can be heated using the heated buffer fluid in a third heat exchanger (3, FIG. 1E), which has a thermal duty that can be in a range between about 15 MW and 25 MW (for example, 21 MW). The third heat exchanger is coupled to, in series with and is downstream of the set of the first and second heat exchangers relative to the buffer fluid flow. As shown in FIG. 1E, the steam heat input for the amine regenerator can be 0 MW because the alternative flow paths disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

The combined buffer fluid exiting the third heat exchanger is then flowed to the gas separation plant 104. A gas separation plant de-ethanizer stream is heated using a portion of the combined heated buffer fluid stream in a fourth heat exchanger (4, FIG. 1F). Also, at the gas separation plant 104, a C3/C4 splitter bottom stream is heated using the remaining portion of the combined heated buffer fluid stream in a fifth heat exchanger (5, FIG. 1F). The fourth heat exchanger (4, FIG. 1F) and the fifth heat exchanger (5, FIG. 1F) are coupled to each other in parallel relative to the flow of buffer fluid. The parallel combination of the fourth heat exchanger (4, FIG. 1F) and the fifth heat exchanger (5, FIG. 1F) is coupled to, in series with and is downstream of the set of the first and second heat exchangers relative to the buffer fluid flow. The thermal duties of the fourth and fifth heat exchangers can range between about 1 MW and 10 MW (for example, 4.3 MW) and about 5 MW and 15 MW (for example, 9.9 MW), respectively. As shown in FIG. 1F, the steam heat input for the gas separation plant de-ethanizer can be 0 MW because the alternative flow paths disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column. Also, as shown in FIG. 1F, the steam heat input for the C3/C4 splitter can be 0 MW because the alternative flow paths disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

In some implementations, the heated buffer fluid can be flowed in series through the different plants. For example, the heated buffer fluid can be flowed first to the gas separation plant then to the sulfur recovery plant. The heated buffer fluid exiting the final exchanger(s) in the series can then be flowed to the buffer fluid tank. The buffer fluid from the buffer fluid tank can then be flowed to the different plants to restart the waste heat recovery and reuse cycle.

The portion of the combined heated buffer fluid exiting the fourth heat exchanger and the remaining portion of the combined heated buffer fluid exiting the fifth heat exchanger are re-combined and flowed to a collection header or the buffer fluid tank.

Such recovery and reuse of waste heat indirectly from the diesel hydrotreating plant can result in decreasing or eliminating the heat energy to heat the sulfur recovery plant or the gas separation plant or a combination of them such as by about 35 MW.

Configuration 2

Figure 1G:
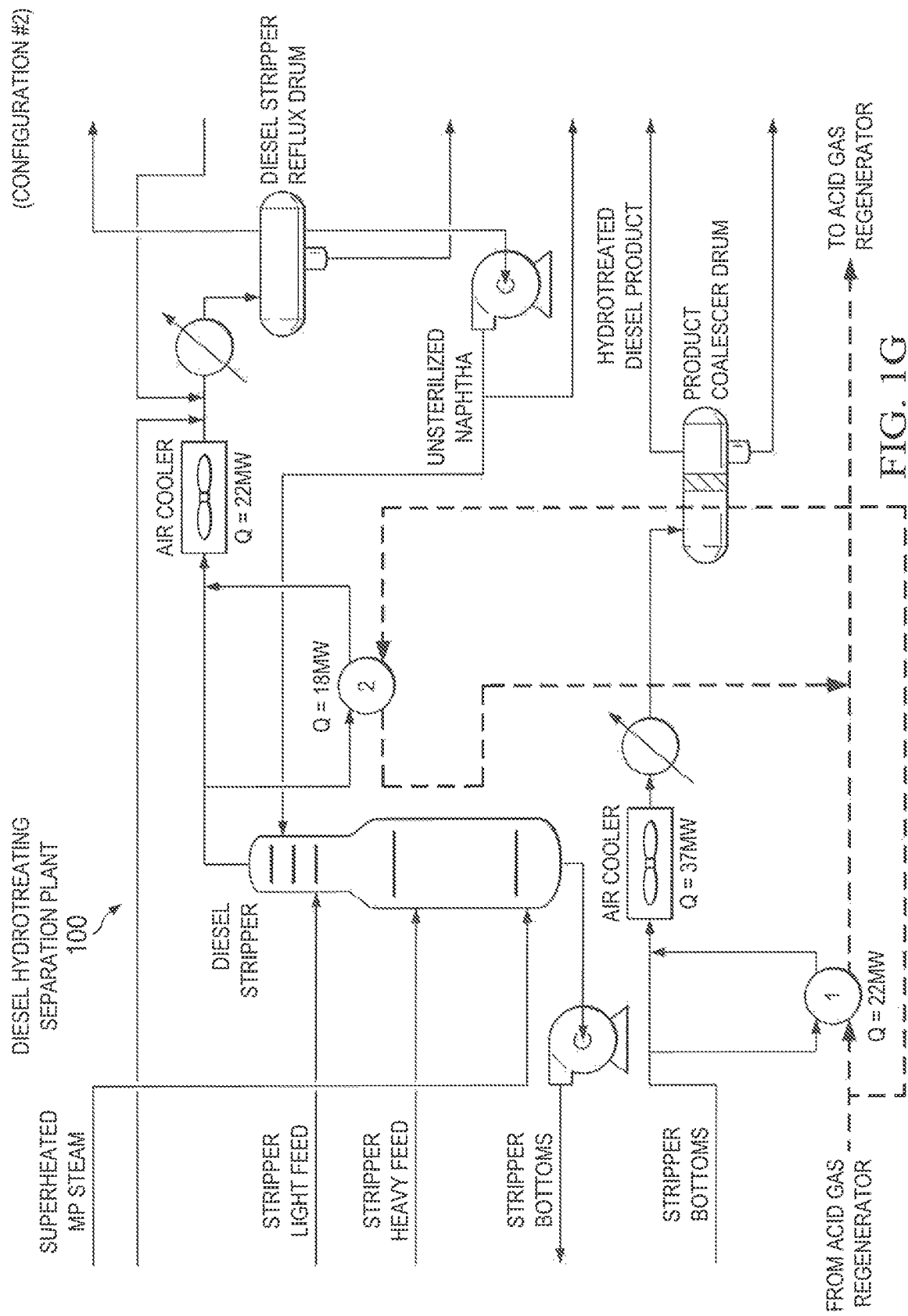
FIGS. 1G-1H illustrate example schematics of a second configuration for heating an amine regeneration plant stream using a diesel hydro-treating plant stream.
Figure 1H:
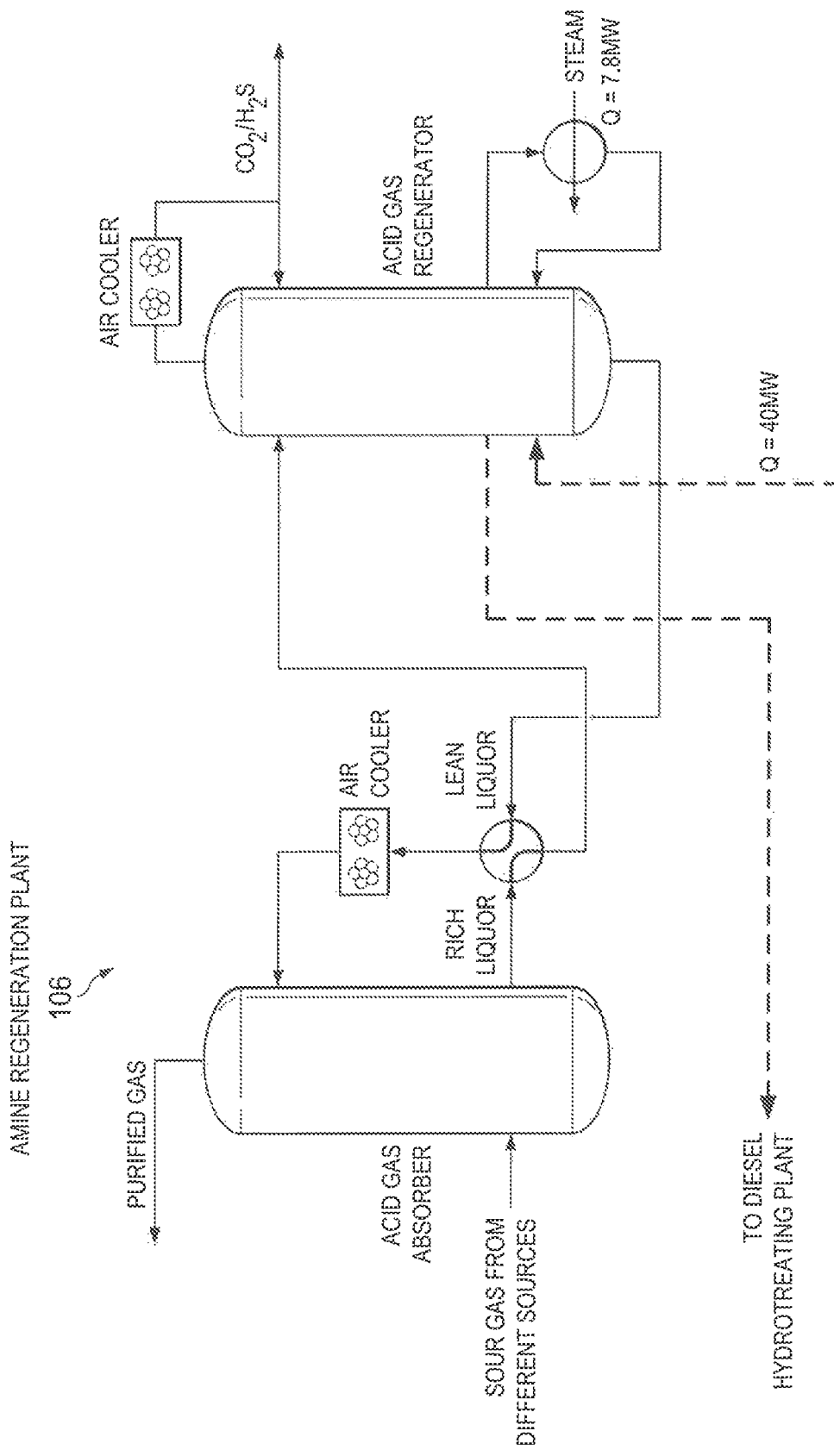

FIGS. 1G and 1H illustrate configurations and related scheme details for directly heating an acid gas regenerator bottom stream in an amine regeneration plant using the diesel hydro-treating plant in the crude oil refining facility. In some implementations, a first stream in a first plant can be directly heated using a multiple second streams in a second plant. In some implementations, the first plant is amine regeneration plant; the first stream is the acid gas regenerator bottoms stream; the second plant is the diesel hydrotreating plant; and the second multiple streams are the diesel stripper overheads and the diesel stripper bottoms streams.

The configurations illustrated in FIGS. 1G and 1H thermally integrate a diesel hydro-treating plant in a crude oil refining facility with an amine regeneration plant in the crude oil refining facility to reduce thermal energy consumption. For example, a reduction in thermal energy consumption by about 40 MW can translate to about 10% of the heating utility consumption in the crude oil facility. As described later, in certain schemes, a process stream (for example, a diesel hydro-treating plant stream or other process streams) can be used to directly heat another process stream (for example, an acid gas regenerator stream or other process stream). In certain configurations, heat exchange between process streams can be implemented using an intermediate buffer fluid, for example, water, oil, or other buffer fluid.

FIG. 1G shows a diesel hydro-treating plant 100 in a crude oil refining facility. FIG. 1H shows an amine regeneration plant 106 in the crude oil refining facility. In some implementations, an acid gas regenerator bottom stream is heated using the diesel hydro-treating plant. The acid gas regenerator bottoms can be flowed into the plant as a single stream and split into multiple streams or it can be flowed into the plant as multiple streams. To do so, a first acid gas regenerator bottoms stream is flowed to and received at the diesel hydro-treating plant 100. The first acid gas regenerator bottoms stream is directly heated using a diesel stripper bottom product stream in a first heat exchanger (1, FIG. 1G). The second acid gas regenerator bottoms stream is directly heated using a diesel stripper overhead stream in a second heat exchanger (2, FIG. 1G). The first and the second heat exchangers are coupled in parallel with one another relative to the flow of acid gas regenerator bottoms. In some implementations, the thermal duties of the two heat exchangers can range between about 10 MW and 20 MW (for example, 18 MW) and 20 MW and 30 MW (for example, 22 MW), respectively. The transfer of heat directly to another process stream captures heat that would have otherwise been discharged to the environment. The diesel stripper overhead stream and the diesel stripper bottoms stream are returned to the diesel hydro-treating plant 100 for further processing.

The heated first and second acid gas regenerator bottoms are then combined and flowed directly into an acid gas regenerator bottom in the amine regeneration plant 106. As shown in FIG. 1H, the steam heat input for the acid gas regenerator can be reduced because the alternative flow paths disclosed in this configuration may in part satisfy the heat load for the operation of the column. In an alternative embodiment, the steam heat input for the acid gas regenerator can be 0 MW because the alternative flow paths disclosed in this configuration may satisfy the entire heat load for the operation of the column.

Such recovery and reuse of waste heat directly from the diesel hydrotreating plant can result in decreasing or eliminating the heat energy to heat the amine regeneration plant or the gas separation plant or a combination of them such as by about 40 MW.

Configuration 3

FIGS. 1I-1L illustrate configurations and related scheme details for heating a gas separation plant stream in a gas separation plant in the crude oil refining facility. In some implementations, a first stream in a first plant can be directly heated using a multiple second streams in a second plant, and multiple third streams in a third plant can be directly heated using a fourth stream in a fourth plant and a fifth stream from the first plant. In some implementations, the first plant is sour water stripper plant; the first stream is the sour water stripper bottoms stream; the second plant is the diesel hydrotreating plant; and the second multiple streams are the diesel stripper overheads and the diesel stripper bottoms streams; the fourth plant is the natural gas steam reforming hydrogen plant; the fourth stream is the low temperature shift (LTS) converter product stream; and the fifth stream is the sour water stripper treated water stream.

The configurations illustrated in FIGS. 1I-1L thermally integrate a diesel hydro-treating plant in a crude oil refining facility with a natural gas steam reforming hydrogen plant, a sour water stripper plant and a gas separation plant in the crude oil refining facility to reduce thermal energy consumption. For example, a reduction in thermal energy consumption by about 44 MW can translate to about 11% of the heating utility consumption in the crude oil facility. As described later, in certain schemes, a process stream (for example, a diesel hydro-treating plant stream or other process streams) can be used to directly heat another process stream (for example, a gas separation plant stream or other process stream). In certain configurations, heat exchange between process streams can be implemented using an intermediate buffer fluid, for example, water, oil, or other buffer fluid.

Figure 1I:
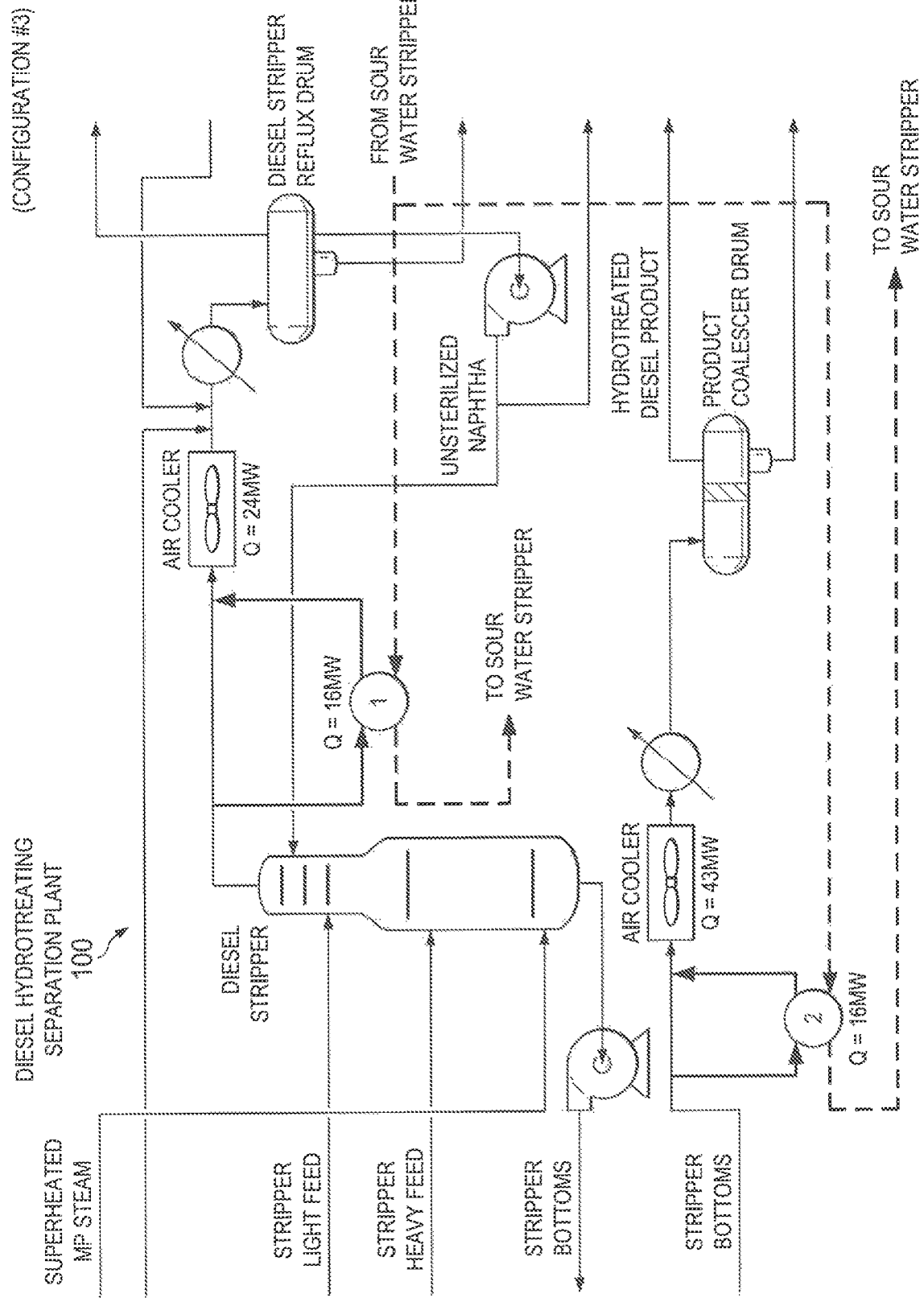
FIGS. 1I-1L illustrate example schematics of a third configuration for heating a sour water stripper plant stream and gas separation plant streams using a diesel hydro-treating plant stream and a hydrogen plant stream.

FIG. 1I shows a diesel hydro-treating plant 100 in a crude oil refining facility. The sour water stripper bottoms stream can be flowed into the plant as a single stream and split into multiple streams or it can be flowed into the plant as multiple streams. In some implementations, a sour water stripper bottoms stream from a sour water stripper plant 110 is flowed to and received at the diesel hydro-treating plant 100. A first sour water stripper bottoms stream is directly heated using a diesel stripper bottom product stream in the diesel hydro-treating plant in a second heat exchanger (2, FIG. 1I). The second sour water stripper bottoms stream is directly heated using a diesel stripper overhead stream in the diesel hydro-treating plant in a first heat exchanger (1, FIG. 1I). The first and the second heat exchangers are coupled in parallel with one another relative to the flow of sour water stripper bottoms. The thermal duty of each of the two heat exchangers can range between about 10 MW and 20 MW (for example, 16 MW). The transfer of heat directly to another process stream captures heat that would have otherwise been discharged to the environment. The diesel stripper overhead stream and the diesel stripper bottoms stream are returned to the diesel hydro-treating plant 100 for further processing.

Figure 1J:
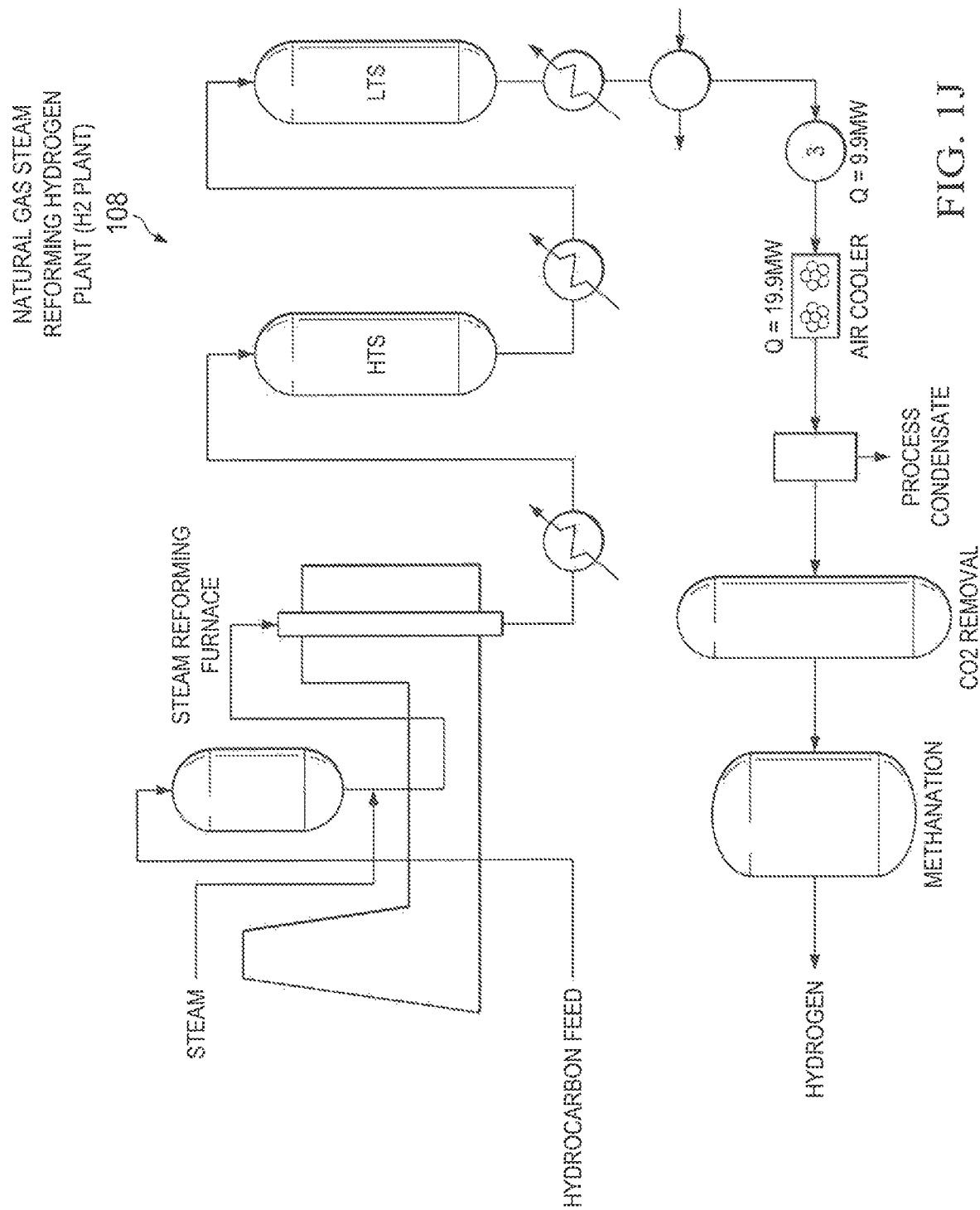
Figure 1K:
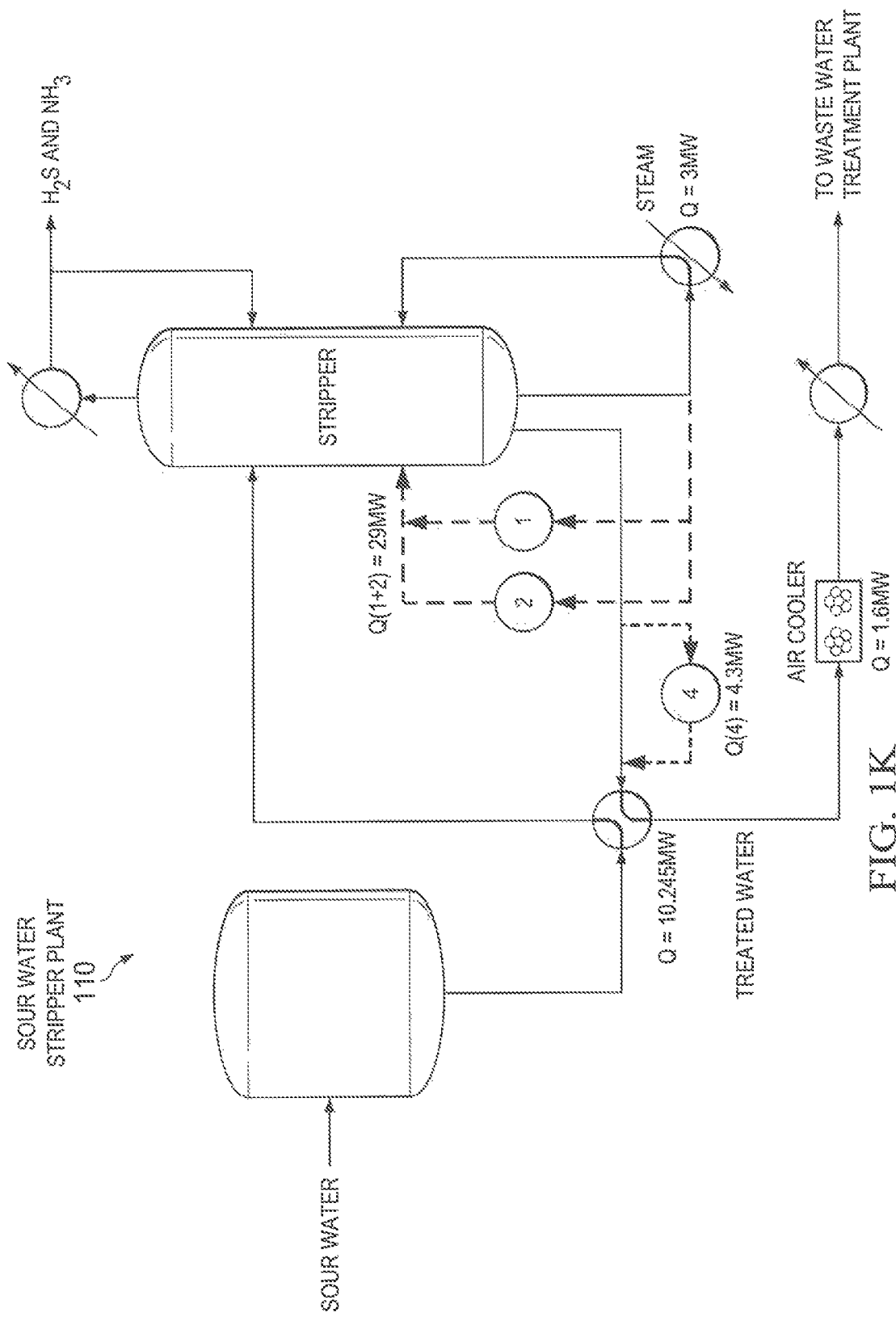

The heated first sour water stripper bottoms stream and the heated second sour water stripper bottoms stream are then flowed to the sour water stripper in the sour water stripper plant 110. As shown in FIG. 1K, the steam heat input for the sour water stripper can be reduced because the alternative flow paths disclosed in this configuration may in part satisfy the heat load for the operation of the column. In an alternative embodiment, the steam heat input for the sour water stripper can be 0 MW because the alternative flow paths disclosed in this configuration may satisfy the entire heat load for the operation of the column.

Figure 1L:
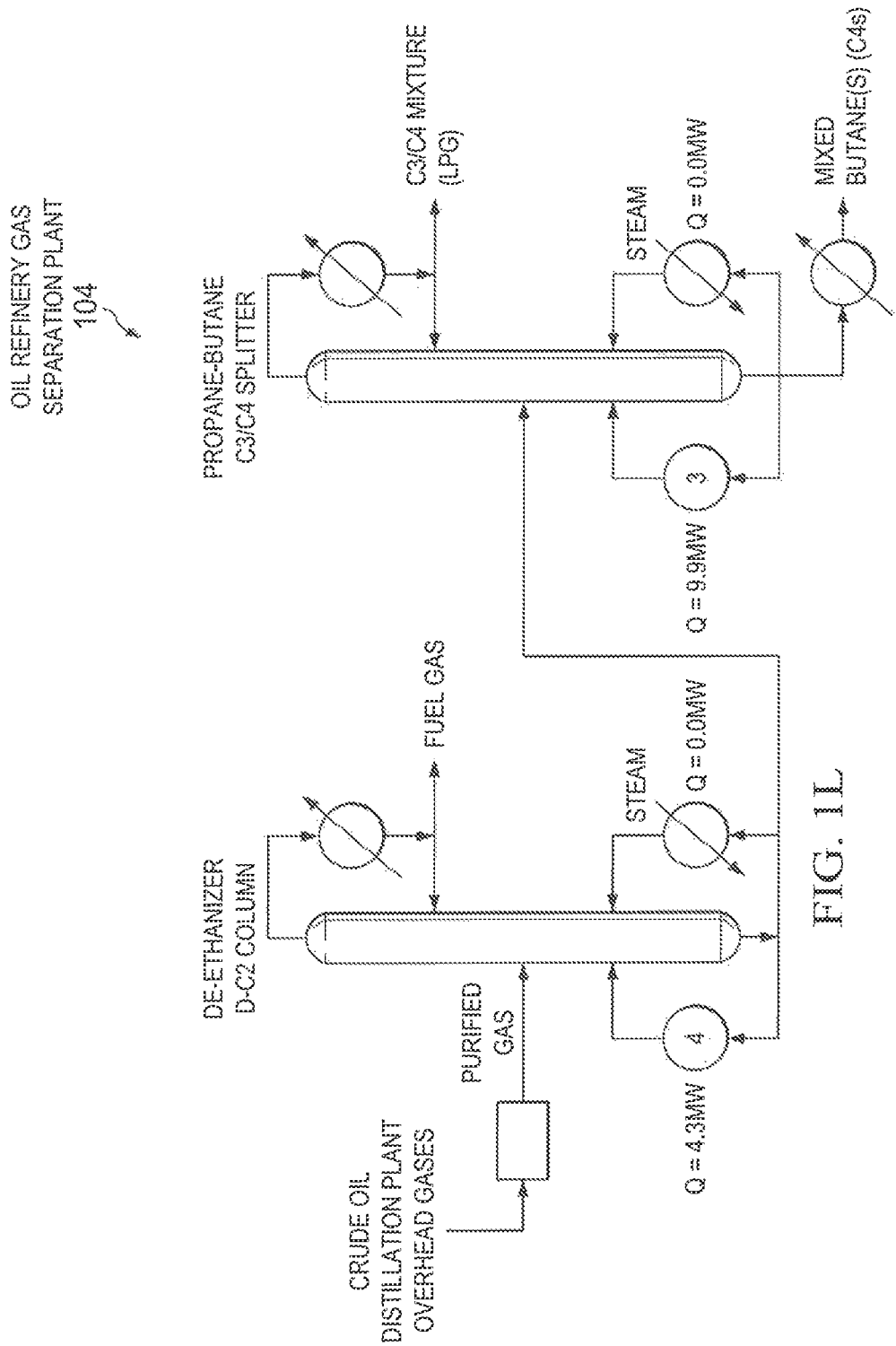

In some implementations, gas plant separation streams are flowed to and received by both the natural gas steam reforming hydrogen plant and the sour water stripper plant. FIG. 1J shows a natural gas steam reforming hydrogen plant 108 in a crude oil refining. FIG. 1L shows a gas separations plant 104 in a crude oil refinery. A first gas separation plant stream, for example, a C3/C4 splitter bottom stream is directly heated using the LTS converter product stream in a third heat exchanger (3, FIG. 1J) with a thermal duty that can range between about 1 MW and 20 MW (for example, 9.9 MW). The transfer of heat directly to another process stream captures heat that would have otherwise been discharged to the environment. The LTS converter product stream is returned to the natural gas steam reforming hydrogen plant 108 for further processing. As shown in FIG. 1L, the steam heat input for the C3/C4 splitter can be 0 MW because the alternative flow paths disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

A second gas separation plant stream, for example, a gas separation plant de-ethanizer bottom stream, from the gas separation plant 104 (FIG. 1L) is heated using the sour water stripper treated water stream in the crude oil refining facility. The gas separation plant de-ethanizer bottom stream is directly heated using a fourth heat exchanger (4, FIG. 1K) with a thermal duty that can range between about 1 MW and 10 MW (for example, 4.3 MW). The transfer of heat directly to another process stream captures heat that would have otherwise been discharged to the environment. The sour water stripper treated water stream is returned to the sour water stripper plant 110 for further processing. As shown in FIG. 1L, in this configuration the steam heat input for the gas separation plant de-ethanizer can be 0 MW because the alternative flow paths disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column.

In this manner, the sour water stripper plant is heated directly using streams from the diesel hydro-treating plant, the gas separation plant is directly heated using streams from the natural gas steam reforming hydrogen plant and the sour water stripper plant. As well, indirectly through the operation of the sour water stripper, the diesel hydro treating plant heats the gas separation plant as the energy introduced into the sour water stripper bottoms stream is in part recovered from the sour water stripper treated water stream. Such recovery and reuse of waste heat directly can result in decreasing or eliminating the heat energy such as by about 44 MW.

Configuration 4

Figure 1M:
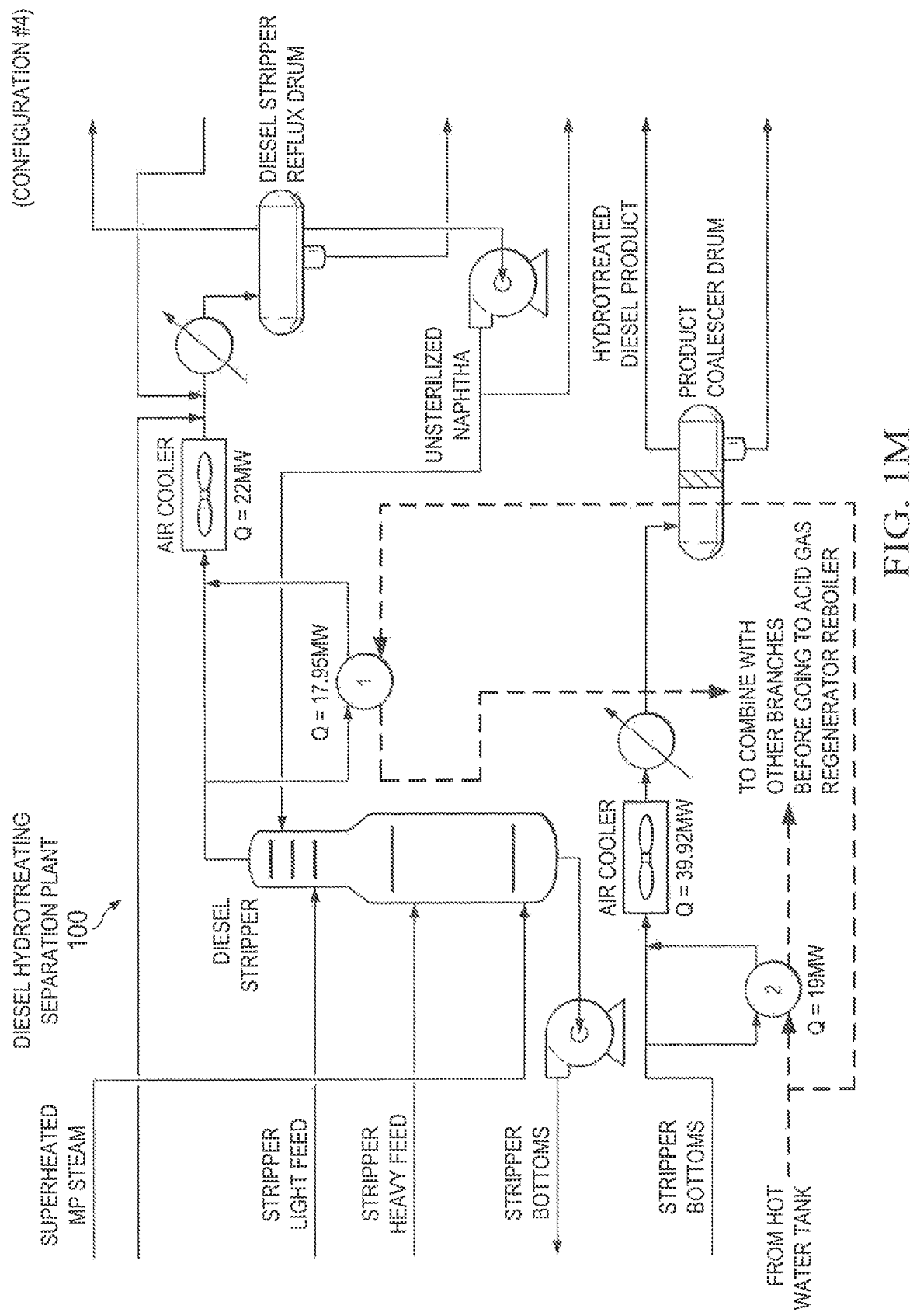
Figure 1N:
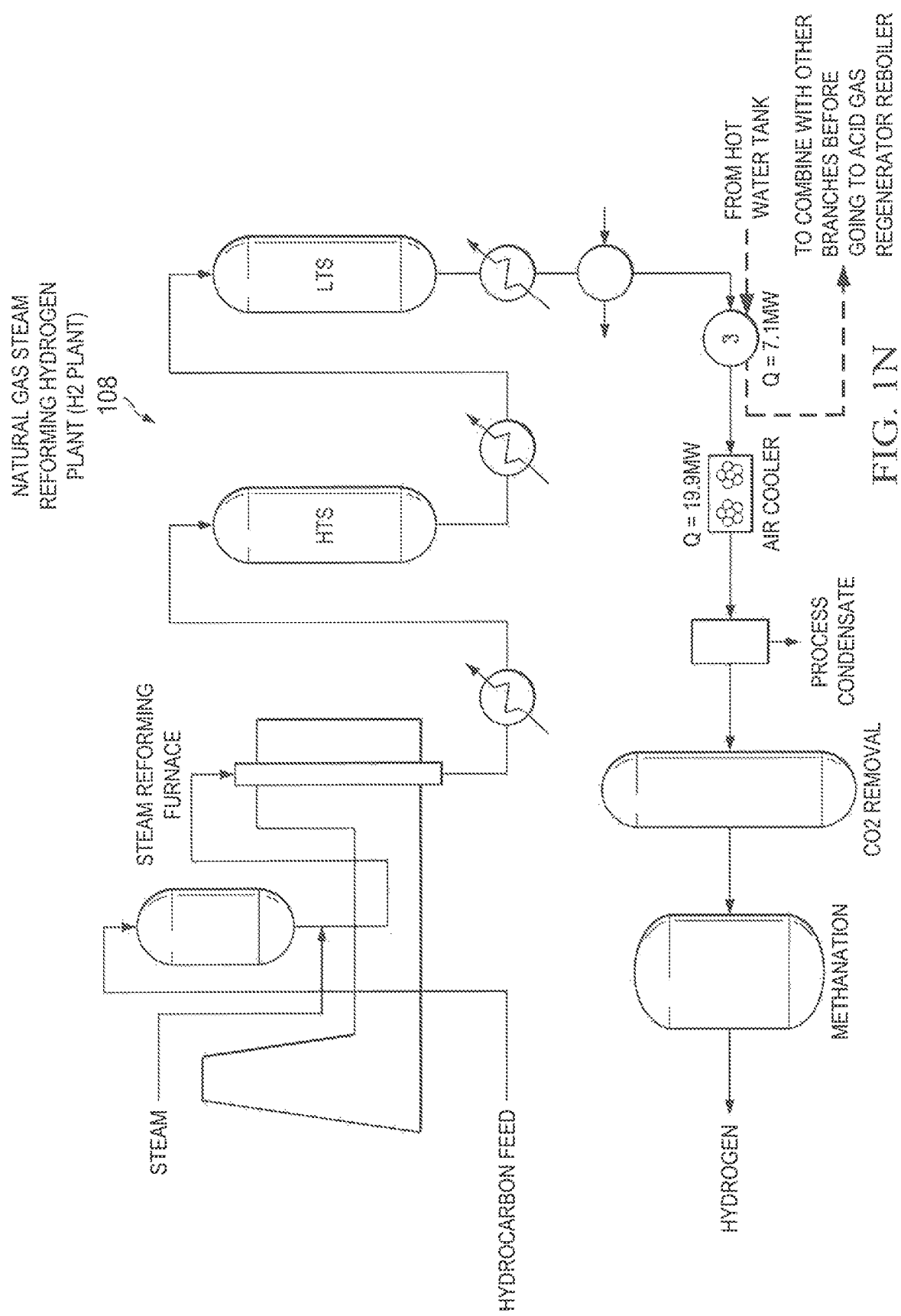
Figure 10:
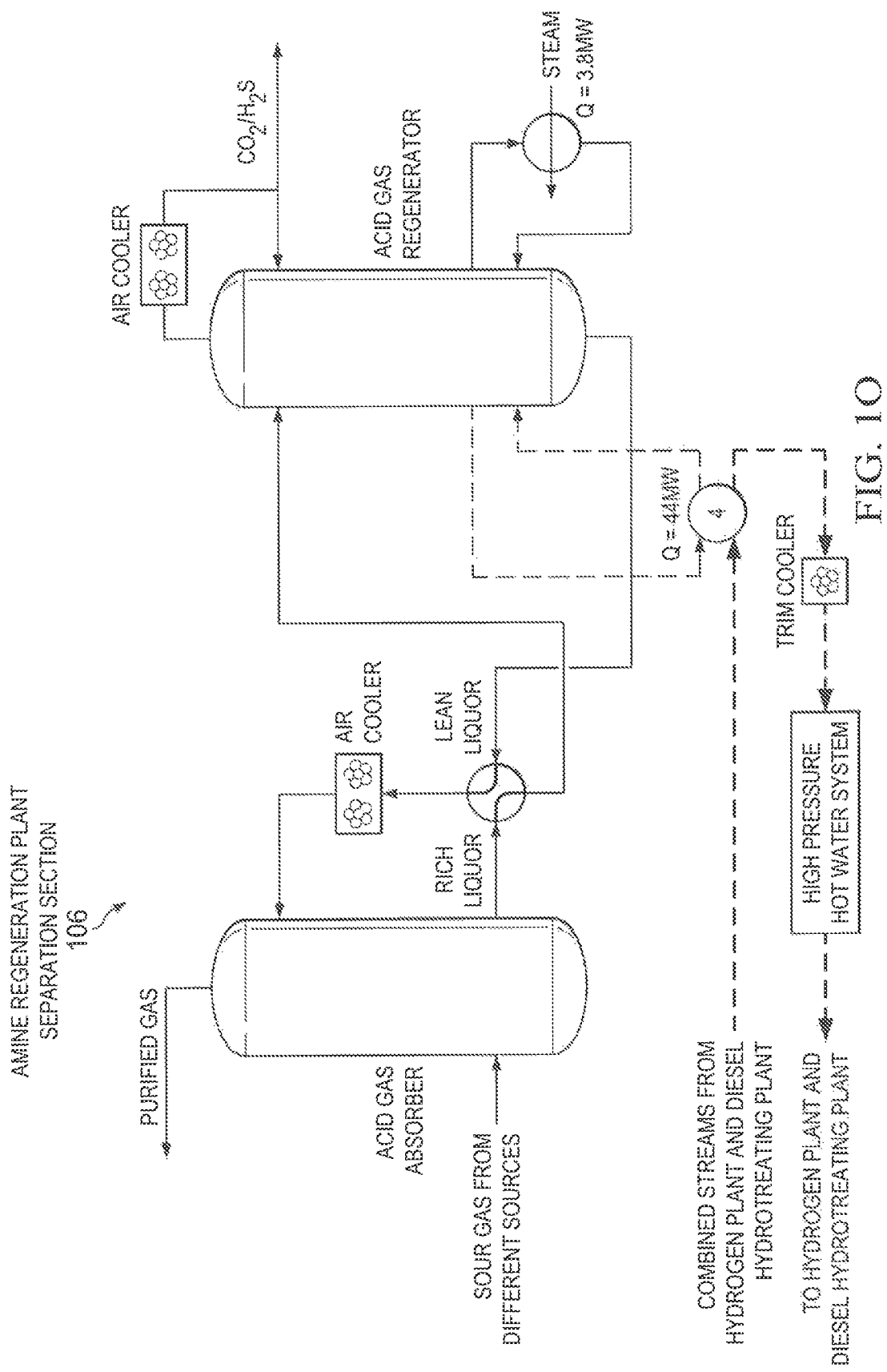

FIGS. 1M-1O illustrate configurations and related scheme details for heating an acid gas regenerator stream in an amine regeneration plant in the crude oil refining facility. In some implementations, a first stream in a first plant can be heated indirectly using multiple second streams in multiple second plants. In some implementations, the first plant is an amine regeneration plant; the first stream is an acid gas regenerator bottoms stream; the multiple second plants include the diesel hydrotreating plant and the natural gas steam reforming hydrogen plant; and the multiple second plant streams include the diesel stripper overheads, the diesel stripper bottoms, and the low temperature shift (LTS) converter product streams.

The configurations illustrated in FIGS. 1M-1O thermally integrate a diesel hydro-treating plant in a crude oil refining facility with a hydrogen plant and an amine regeneration plant in the crude oil refining facility to reduce thermal energy consumption. For example, a reduction in thermal energy consumption by about 44 MW can translate to about 11% of the heating utility consumption in the crude oil facility. As described later, in certain schemes, a process stream (for example, a diesel hydro-treating plant stream or other process streams) can be used to indirectly heat another process stream (for example, an amine regeneration plant stream or other process stream). In certain configurations, heat exchange between process streams can be implemented using an intermediate buffer fluid, for example, water, oil, or other buffer fluid.

A buffer fluid (for example, high pressure water) from a buffer fluid tank (for example, hot water tank) is flowed to the diesel hydro-treating plant 100 and to the natural gas steam reforming hydrogen plant 108. The buffer fluid can be flowed into a plant as a single stream and split into multiple streams or it can be flowed into the plant as multiple streams.

FIG. 1M shows a diesel hydro-treating plant 100 in a crude oil refining facility. In some implementations, a buffer fluid (for example, oil, water or other buffer fluid) is received, for example, from a buffer fluid tank, at the diesel hydro-treating plant 100. The first buffer fluid stream is heated using a diesel stripper overhead stream in a first heat exchanger (1, FIG. 1M), which has a thermal duty that can range between about 15 MW and 25 MW (for example, 17.95 MW). The second buffer fluid stream is heated using a diesel stripper bottom product stream in the diesel hydro-treating plant 100 in a second heat exchanger (2, FIG. 1M), which has a thermal duty that can range between about 15 MW and 25 MW (for example, 19 MW). The first and the second heat exchangers are coupled in parallel with one another relative to the flow of buffer fluid. For both of these streams, the transfer of heat into the buffer fluid captures heat that would have otherwise been discharged to the environment. Both the diesel stripper bottom product stream and the diesel stripper overhead stream are returned to the diesel hydrotreating plant 100 for further processing.

FIG. 1N shows a natural gas steam reforming hydrogen plant 108 in a crude oil refining facility. In some implementations, a third buffer fluid (for example, oil, water or other buffer fluid) is received, for example, from a buffer fluid tank, is also flowed to a natural gas steam reforming hydrogen plant 108. The third buffer fluid is heated using a low temperature shift (LTS) converter product stream, for example, using a third heat exchanger (3, FIG. 1N), which has a thermal duty that can range between about 5 MW and 15 MW (for example, 7.1 MW). The third heat exchanger is coupled in parallel with the first and second heat exchangers relative to the flow of buffer fluid. The transfer of heat from this process stream into the buffer fluid captures heat that would have otherwise been discharged to the environment. The LTS converter product is returned to the natural gas steam reforming hydrogen plant 108 for further processing.

The heated first buffer fluid, the heated second buffer fluid, and the heated third buffer fluid are combined into a combined heated buffer fluid stream in a collection header (or in some embodiments, a heated or insulated buffer fluid tank or storage unit that can hold heated collected buffer fluid for a period before use) that is flowed into the amine regeneration plant 106.

FIG. 1O shows the amine regeneration plant 106 in a crude oil refining facility. An acid gas regenerator bottoms stream is heated using the combined heated buffer fluid in a fourth heat exchanger (4, FIG. 1O), which has a thermal duty that can range between about 40 MW and 50 MW (for example, 44 MW). The fourth heat exchanger is coupled to, in series with and is downstream of the set of the first, second and third heat exchangers relative to the buffer fluid flow. As shown in FIG. 1O, the steam heat input for the acid gas regenerator can be 0 MW because the alternative flow paths disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

As shown in FIG. 1O, the combined heated buffer fluid stream exiting the fourth heat exchanger is flowed to a collection header or the buffer fluid tank to repeat the waste heat recovery and reuse processes.

Such recovery and reuse of waste heat indirectly from both the diesel hydrotreating plant and the natural gas steam reforming hydrogen plant can result in decreasing or eliminating the heat energy to heat the amine regeneration plant such as by about 44 MW.

Configuration 5

FIGS. 1P-1W illustrate configurations and related scheme details for heating a streams both in a gas separation plant and a sour water stripper plant in the crude oil refining facility. The configurations illustrated in FIGS. 1P-1W thermally integrate a diesel hydro-treating plant, a natural gas steam reforming hydrogen plant, the sour water stripper plant and the gas separation plant to reduce thermal energy consumption. For example, a reduction in thermal energy consumption by about 46 MW can translate to about 11% of the heating utility consumption in the crude oil facility. As described later, in certain schemes, a process stream (for example, a natural gas steam reforming hydrogen plant (H2 plant) stream or other process streams) can be used to directly heat another process stream (for example, a gas separation plant stream or other process stream). In certain configurations, heat exchange between process streams can be implemented using an intermediate buffer fluid, for example, water, oil, or other buffer fluid.

Configuration 5—Scheme A

In some implementations described with reference to FIGS. 1P-1S, streams in the gas separation plant and the sour water stripper plant can be heated directly using the diesel hydro-treating plant and the natural gas steam reforming hydrogen plant. In some implementations, a first stream in a first plant can be directly heated using multiple second streams from multiple second plants, and multiple third streams in a third plant can be directly heated using one of the second streams from one of the second plants. In some implementations, the first plant is the sour water stripper plant; the first stream is the sour water stripper bottoms stream; the multiple second plants are the natural gas steam reforming hydrogen gas plant and the diesel hydrotreater plant; the multiple second streams are the low temperature shift (LTS) converter product stream, the diesel stripper overheads and diesel stripper bottoms streams; the third plant is the gas separations plant; and the multiple streams in the third plant include the de-ethanizer bottoms stream and the C3/C4 splitter bottoms stream. The second plant that heats the third plant is the natural gas steam reforming hydrogen plant. The second stream that heats the third streams is the LTS converter product stream.

Figure 1P:
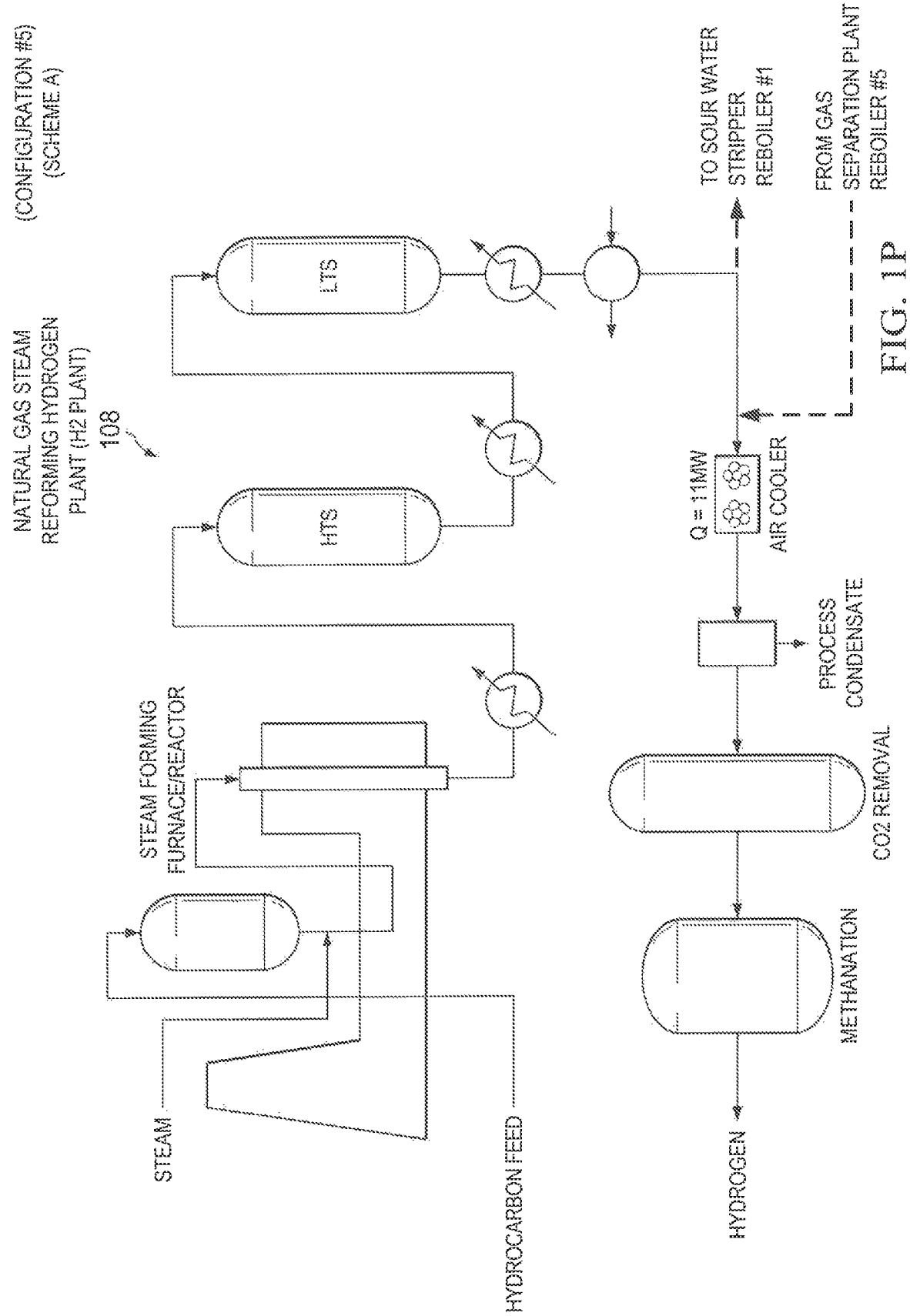
FIGS. 1P-1W illustrate example schematics of a fifth configuration for heating a sour water stripper plant stream and gas separation plant streams using a diesel hydro-treating plant stream and a hydrogen plant stream.
Figure 1Q:
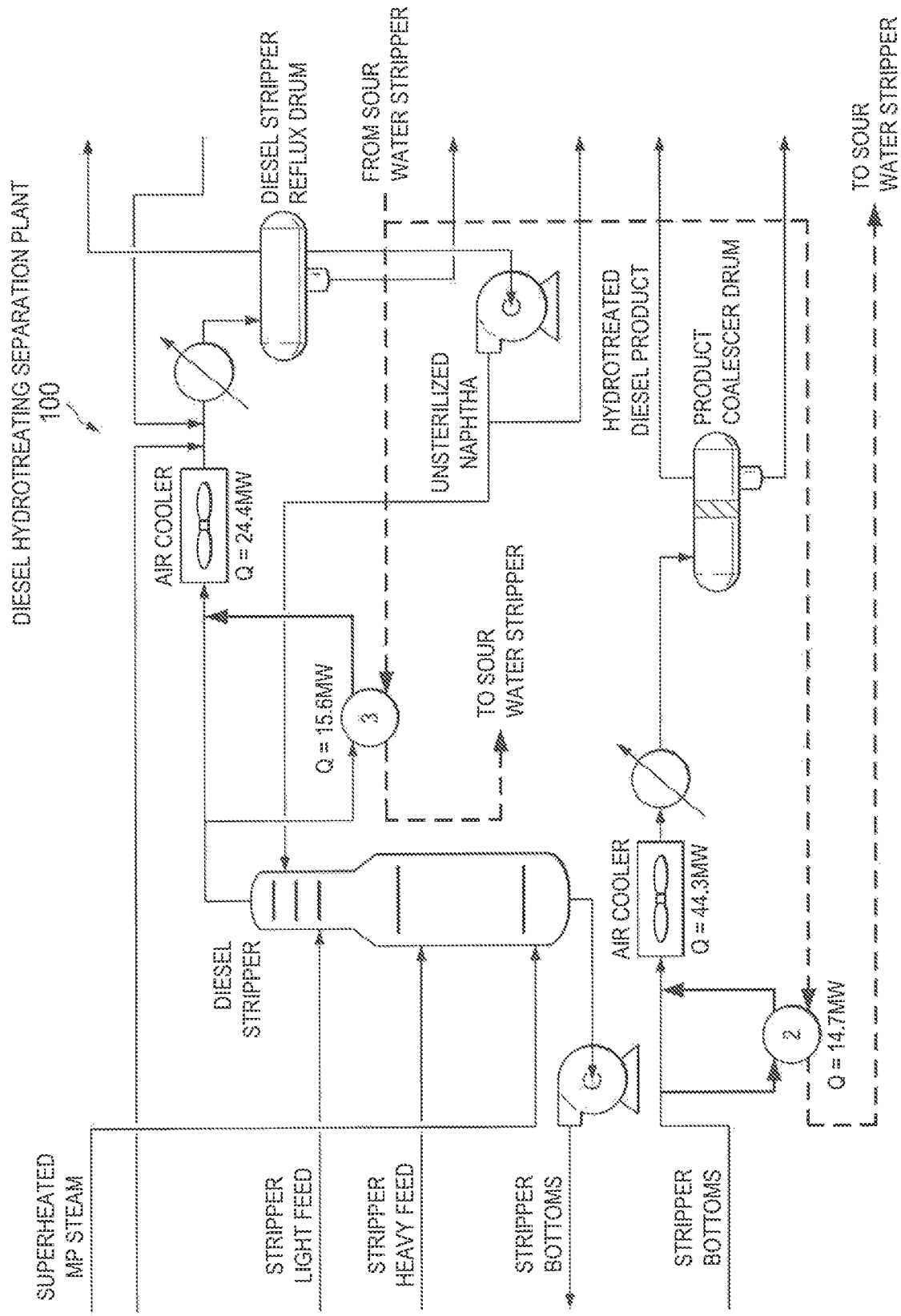

FIG. 1Q shows a diesel hydro-treating plant 100 in a crude oil refining facility. The sour water stripper bottoms stream can be flowed into the plant as a single stream and split into multiple streams or it can be flowed into the plant as multiple streams. The sour water stripper bottoms stream is split into a first, a second and a third stream. The first sour water stripper bottoms stream is directly heated using a diesel stripper bottom product stream in a second heat exchanger (2, FIG. 1Q). The second sour water stripper bottoms stream is heated using a diesel stripper overhead stream in a third heat exchanger (3, FIG. 1Q). The second and third heat exchangers are coupled in parallel with one another relative to the flow of sour water stripper bottoms. The thermal duties of the two heat exchangers can each range between about 10 MW and 20 MW (for example, 14.7 MW and 15.6 MW, respectively). The transfer of heat directly to another process stream captures heat that would have otherwise been discharged to the environment. Both the diesel stripper bottom product stream and the diesel stripper overhead stream are returned to the diesel hydrotreating plant 100 for further processing.

Figure 1R:
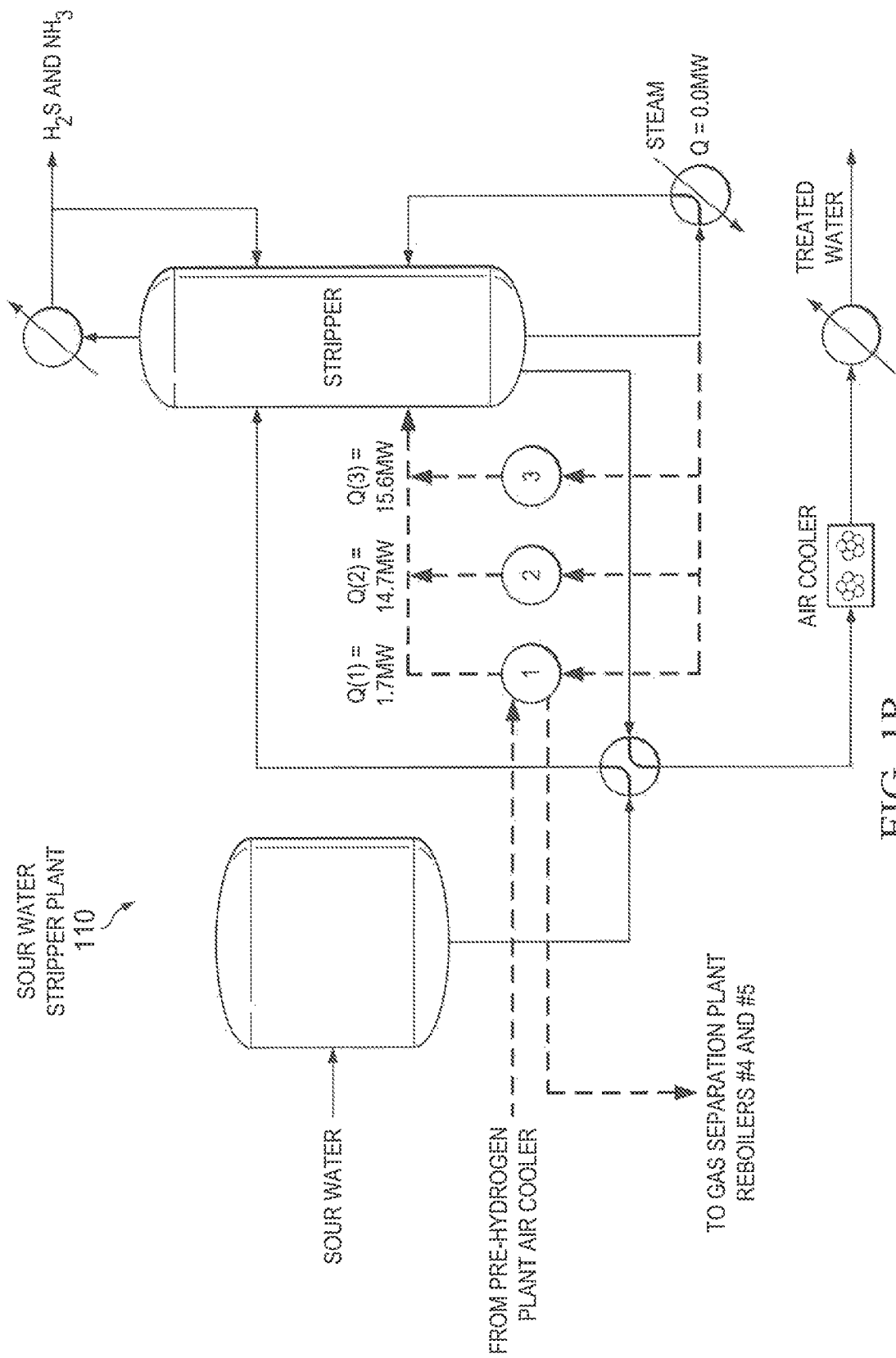

FIG. 1P shows a natural gas steam reforming hydrogen plant 108 in the crude oil refining facility. FIG. 1R shows a sour water stripper plant 110 in the crude oil refining facility. A third sour water stripper bottoms stream from the sour water plant 110 is flowed to and directly heated using low temperature shift (LTS) converter product stream in a first heat exchanger (1, FIG. 1R), which has a thermal duty that can range between about 1 MW and 10 MW (for example, 1.7 MW). The transfer of heat directly to another process stream captures heat that would have otherwise been discharged to the environment.

The heated sour water stripper bottoms streams from the first, the second and the third heat exchangers are combined and flowed into the sour water stripper in the sour water stripper plant 110. FIG. 1R shows a schematic of the sour water stripper bottoms streams being heated by the first, second and third heat exchangers. The first, second and third heat exchangers are coupled in parallel with one another relative to the flow of sour water stripper bottoms. As shown in FIG. 1R, the steam heat input for the sour water stripper can be 0 MW because the alternative flow paths disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Figure 1S:
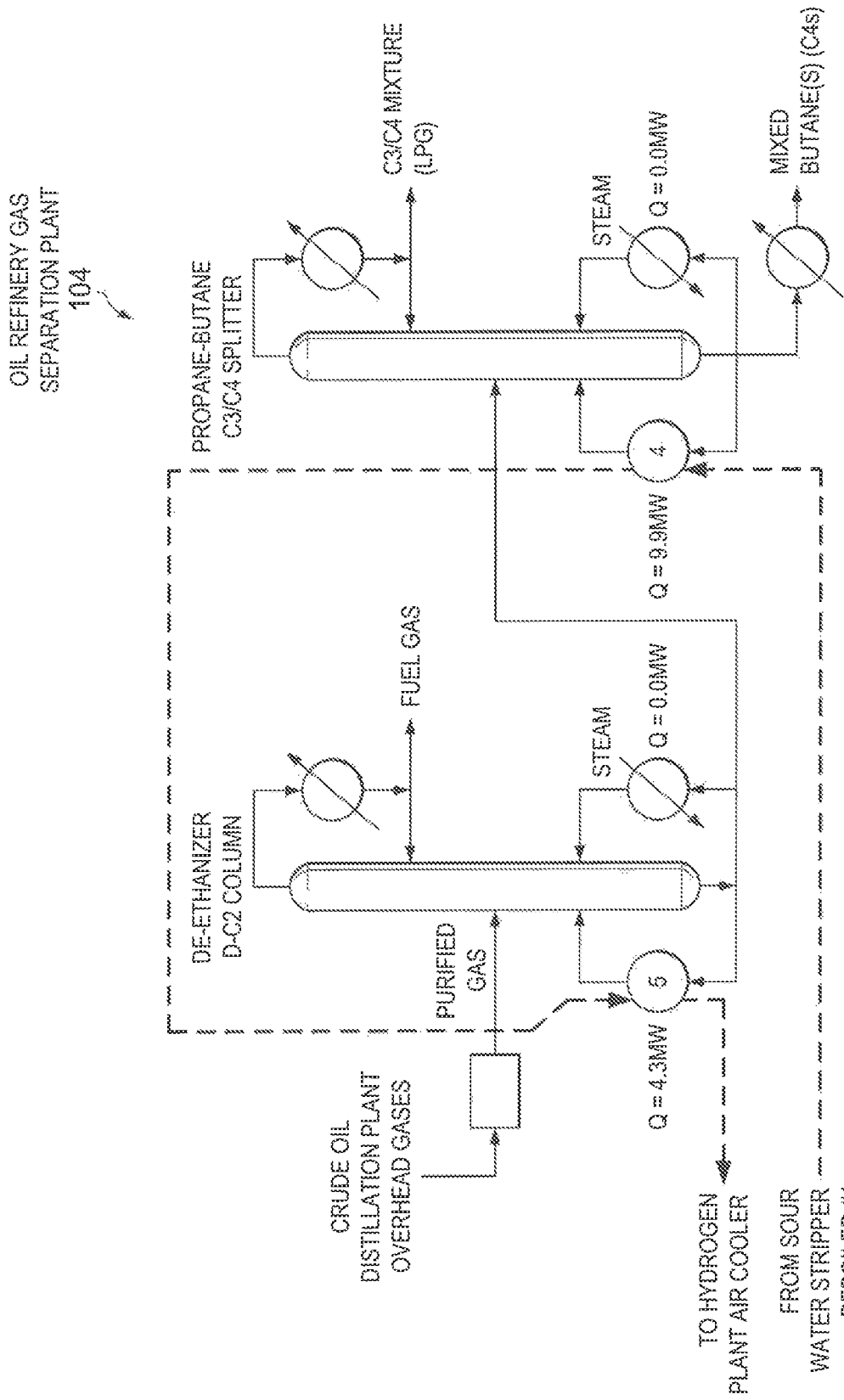

After heating a portion of the sour water stripper bottoms in the first heat exchanger, the partially-cooled LTS product stream is flowed to the gas separation plant 104. At the gas separation plant 104, the partially-cooled LTS product stream is used to directly heat a C3/C4 splitter using a fourth heat exchanger (4, FIG. 1S) with a thermal duty that can range between about 5 MW and 15 MW (for example, 9.9 MW). The fourth heat exchanger is coupled to, downstream of and in series with the first heat exchanger relative to the LTS converter product stream flow. The transfer of heat directly to another process stream captures heat that would have otherwise been discharged to the environment. As shown in FIG. 1S, the steam heat input for the C3/C4 splitter can be 0 MW because the alternative flow paths disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

Also as shown in FIG. 1S, at the gas separation plant 104, the partially-cooled LTS converter product stream exiting the fourth heat exchanger (4, FIG. 1S) is used to directly heat a de-ethanizer reboiler using a fifth heat exchanger (5, FIG. 1S), which has a thermal duty that can range between about 1 MW and 10 MW (for example, 4.3 MW). The fifth heat exchanger is coupled to, downstream of and in series with the fourth heat exchanger relative to the LTS converter product stream flow. The first, fourth and fifth heat exchangers are coupled in series with one another relative to the flow of the LTS product flow. The transfer of heat directly to another process stream captures heat that would have otherwise been discharged to the environment. As shown in FIG. 1S, the steam heat input for the de-ethanizer can be 0 MW because the alternative flow paths disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column. The LTS converter product stream exiting the fifth heat exchanger is returned to the natural gas steam reforming hydrogen plant 108 for further processing (FIG. 1P).

In some implementations, the LTS converter product can be flowed in series through the different plants. For example, the LTS converter product can be flowed first to the sour water stripper plant and then to the gas separations plant. In another embodiment, the LTS converter product within the gas separation plant stream may flow in a different order as described previously. The heated buffer fluid exiting the final exchanger(s) in the series can then be flowed to the buffer fluid tank. The buffer fluid from the buffer fluid tank can then be flowed to the different plants to restart the waste heat recovery and reuse cycle.

In this manner, the sour water stripper is directly heated using both the natural gas steam reforming hydrogen plant and the diesel hydro-treating plant, and the gas separation plant is heated directly using the natural gas steam reforming hydrogen plant. Such recovery and reuse of waste heat directly from both the diesel hydrotreating plant and the natural gas steam reforming hydrogen plant can result in decreasing or eliminating the heat energy to heat the sour water stripper plant or the gas separation plant or a combination of them such as by about 46 MW.

Configuration 5—Scheme B

In some implementations described with reference to FIGS. 1T-1W, the gas separation plant and the sour water stripper can be heated indirectly using the diesel hydro-treating plant and the natural gas stream reforming hydrogen plant. In some implementations, multiple first streams in multiple first plants can be heated indirectly using multiple second streams in multiple second plants. In some implementations, the first plants are a sour water stripper plant and a gas separation plant; the first streams are a sour water stripper bottoms, a de-ethanizer bottoms and a C3/C4 splitter bottoms streams; the multiple second plants include the diesel hydrotreating plant and the natural gas steam reforming hydrogen plant; and the multiple second plant streams include the diesel stripper overheads, the diesel stripper bottoms, and the low temperature shift (LTS) converter product streams.

A buffer fluid (for example, high pressure water) from a buffer fluid tank (for example, hot water tank) is flowed to the diesel hydro-treating plant 100 and to the natural gas stream reforming hydrogen plant 108. The buffer fluid can be flowed into a plant as a single stream and split into multiple streams or it can be flowed into the plant as multiple streams.

Figure 1T:
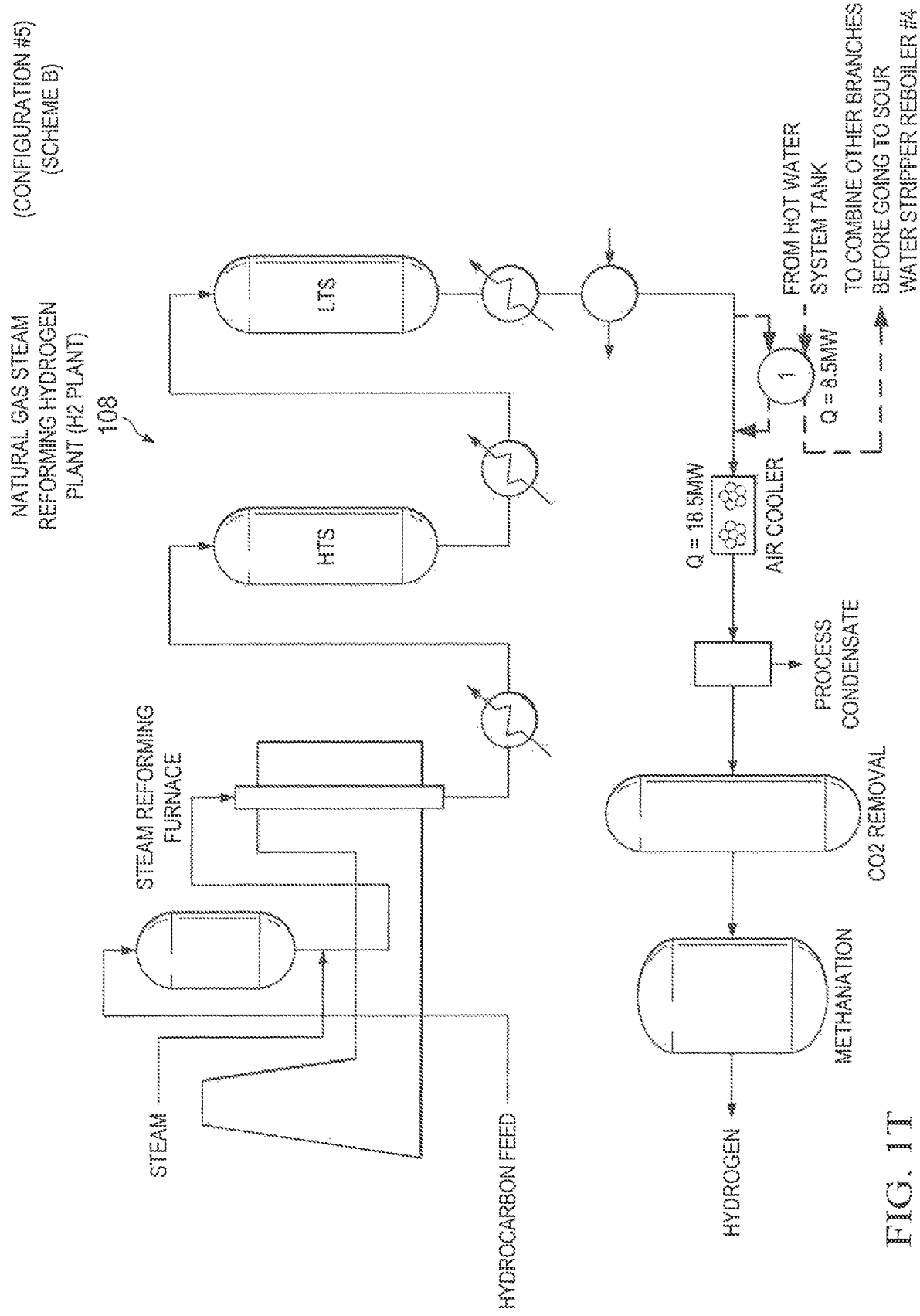
Figure 1U:
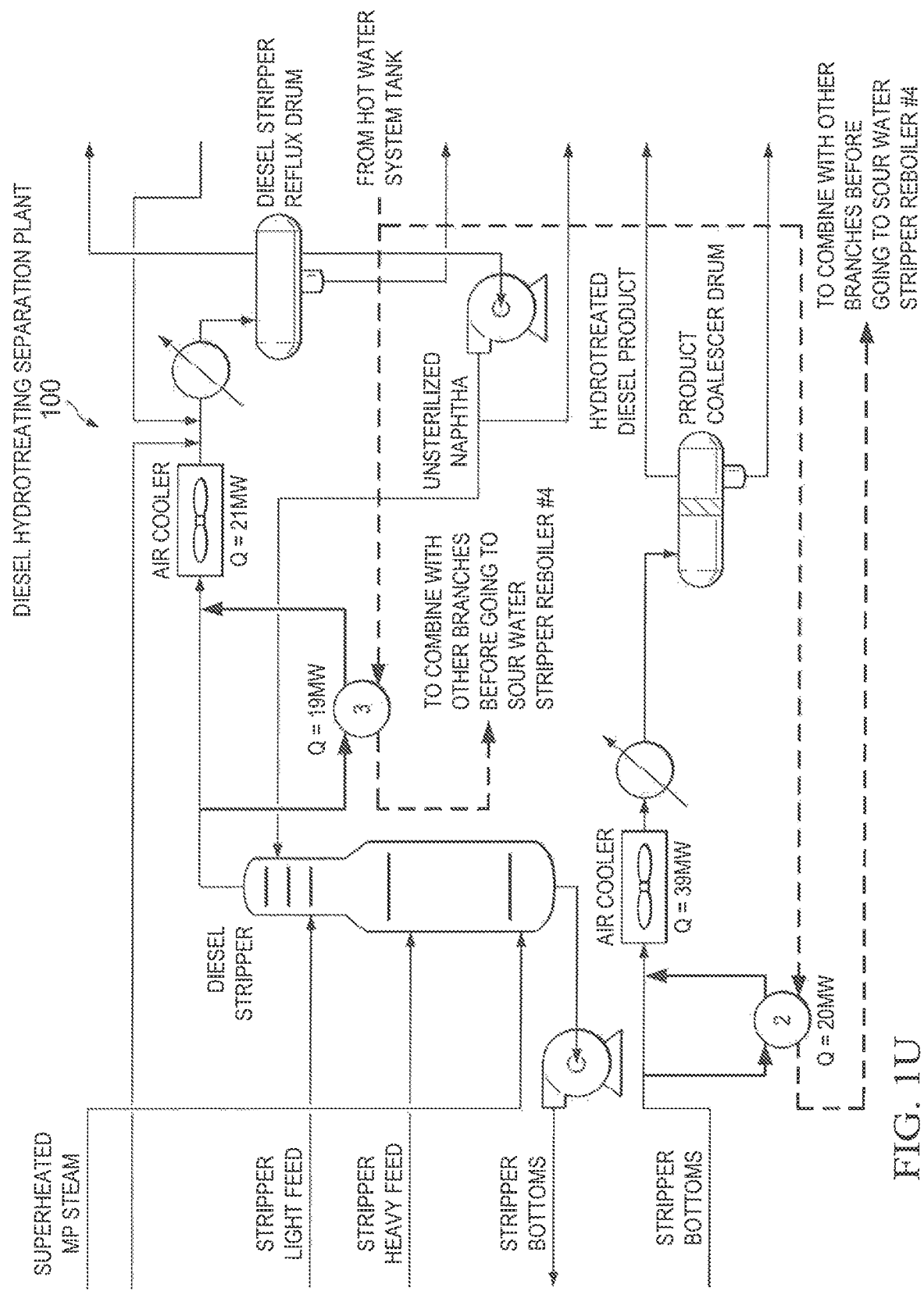

FIG. 1U shows a diesel hydro-treating plant 100 in the crude oil refining facility. A first buffer fluid stream is heated using a diesel stripper bottom product stream in a second heat exchanger (2, FIG. 1U), which has a thermal duty that can range between about 15 MW and 25 MW (for example, 20 MW). A second buffer fluid stream is heated using a diesel stripper overhead stream in the diesel hydro-treating plant 100 in a third heat exchanger (3, FIG. 1U), which has a thermal duty that can range between about 15 MW and 25 MW (for example, 19 MW). The second and the third heat exchangers are coupled in parallel with one another relative to the flow of the buffer fluid. For both of these process streams, the transfer of heat into the buffer fluid captures heat that would have otherwise been discharged to the environment. Both the diesel stripper bottom product stream and the diesel stripper overhead stream are returned to the diesel hydrotreating plant 100 for further processing.

FIG. 1T shows a natural gas steam reforming hydrogen plant 108 in the crude oil refining facility. A third buffer fluid stream is heated using a low temperature shift (LTS) converter product stream in a first heat exchanger (1, FIG. 1T), which has a thermal duty that can range between about 5 MW and 15 MW (for example, 8.5 MW). The first, second and the third heat exchangers are coupled in parallel with one another relative to the flow of the buffer fluid. The LTS converter product stream is returned to the natural gas steam reforming hydrogen plant 108 for further processing.

The heated first buffer fluid stream, the heated second buffer fluid stream, and the third heated buffer fluid stream are combined into a combined heated buffer fluid in a collection header (or in some embodiments, a heated or insulated buffer fluid tank or storage unit that can hold heated collected buffer fluid for a period before use) that can be flowed to a gas separation plant 104 or a sour water stripper plant 110.

Figure 1V:
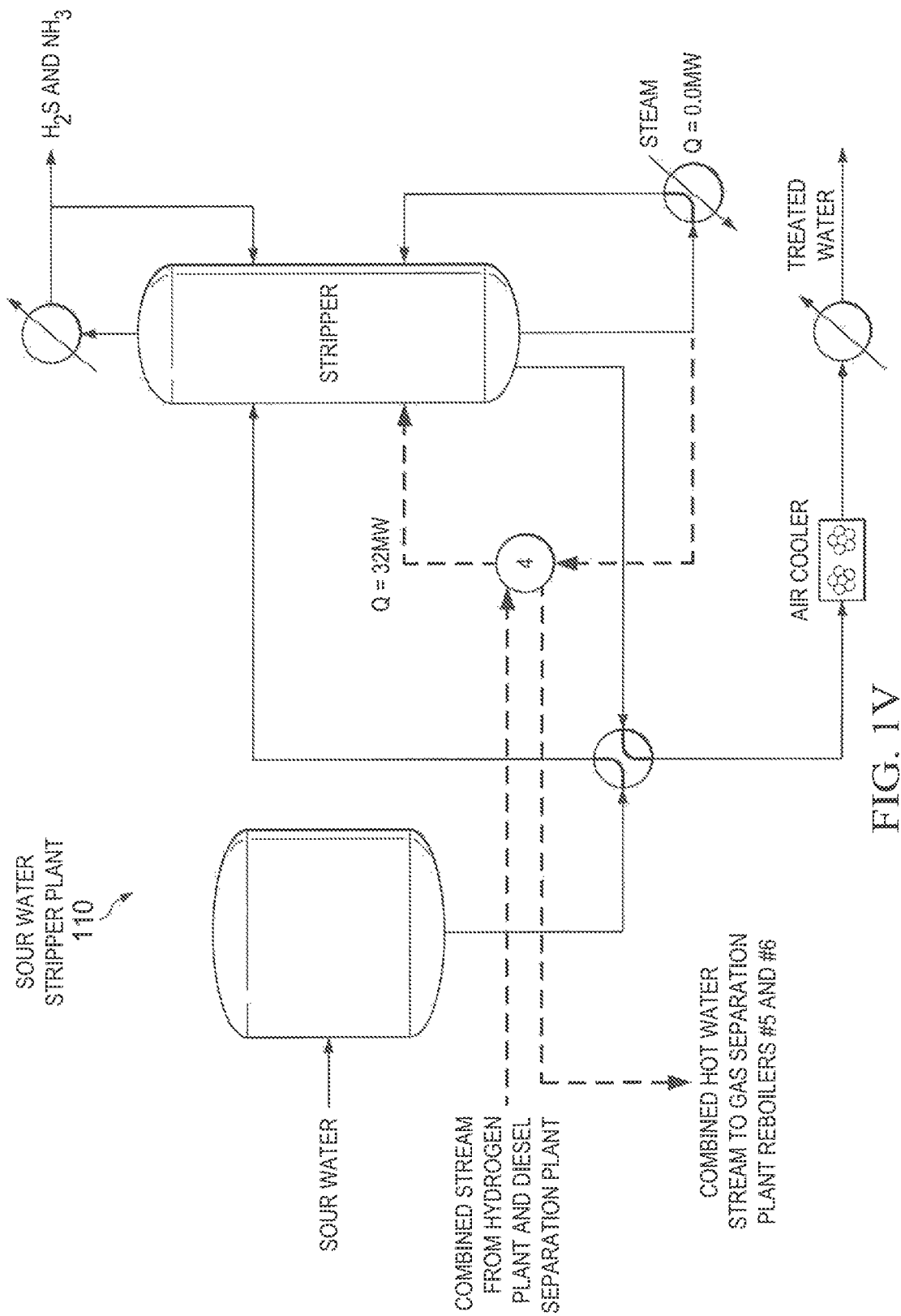

In an embodiment, the buffer fluid is flowed to the sour water stripper plant 110. FIG. 1V shows the sour water stripper plant 110 in a crude oil refining facility. The sour water stripper plant bottom stream is heated using the combined heated buffer fluid using a fourth heat exchanger (4, FIG. 1V), which has a thermal duty that can range between about 25 MW and 35 MW (for example, 32 MW). The fourth heat exchanger is coupled to, in series with and is downstream of the set of the first, second and third heat exchangers relative to the flow of buffer fluid. As shown in FIG. 1V, the steam heat input for the sour water stripper can be 0 MW because the alternative flow paths disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Figure 1W:
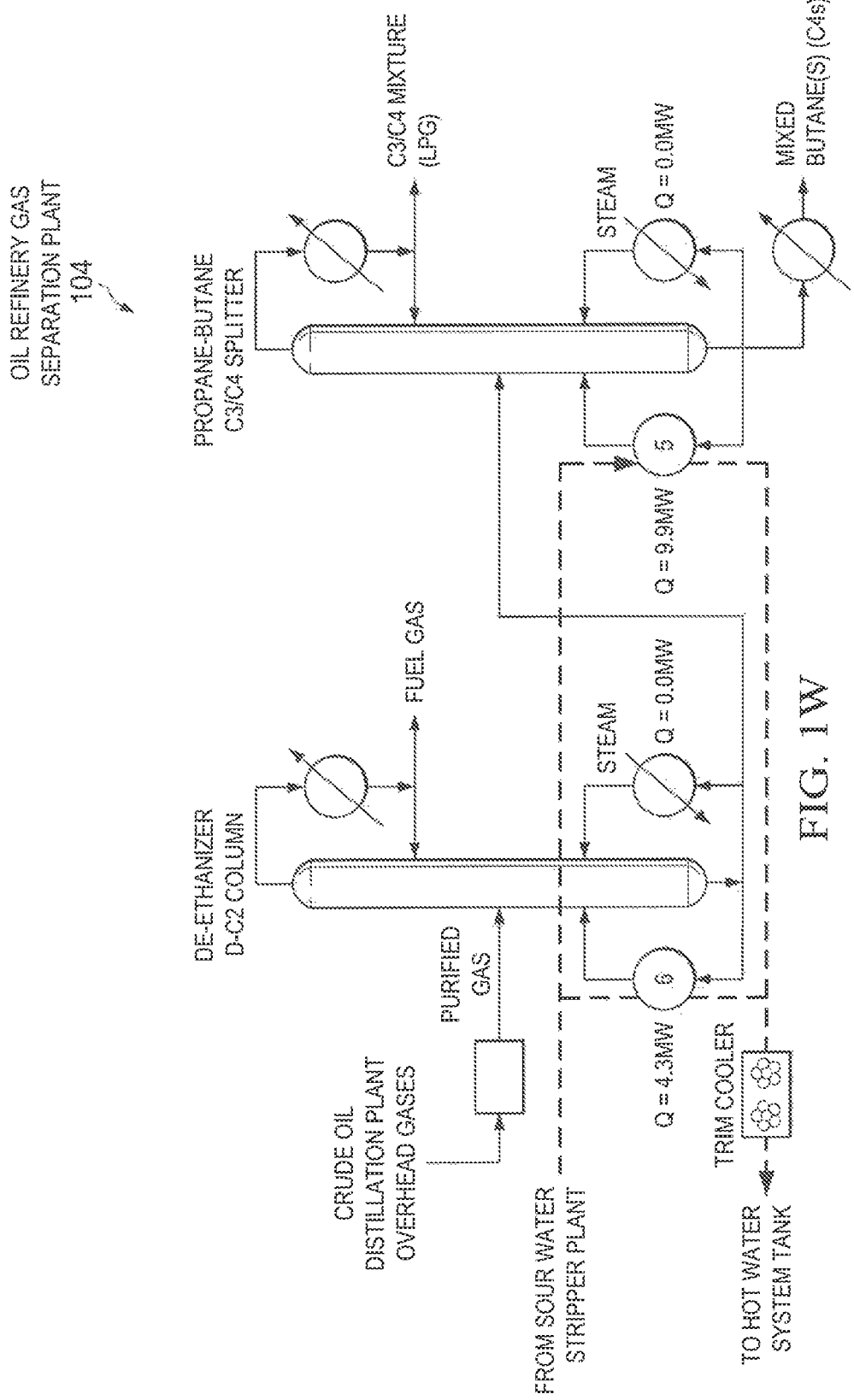

The combined heated buffer fluid exiting the fourth heat exchanger is then flowed to the gas separation plant 104 as shown in FIG. 1W. At the gas separation plant 104, the combined heated buffer fluid is split into two heated buffer fluid streams. A first portion of the heated buffer fluid streams is used to heat a C3/C4 splitter in the gas separation plant 104 using a fifth heat exchanger (5, FIG. 1W), which has a thermal duty that can range between 5 MW and 15 MW (for example, 9.9 MW). The remaining portion of the heated buffer fluid streams is used to heat a de-ethanizer reboiler in the gas separation plant 104 using a sixth heat exchanger (6, FIG. 1W), which has a thermal duty that can range between about 1 MW and 10 MW (for example, 4.3 MW). The set of fifth and the sixth heat exchangers are coupled in parallel to one another in relation to the buffer fluid flow. In addition, the set of fifth and sixth heat exchangers are coupled to, in series with and are downstream of the set of first, second and third heat exchangers relative to the flow of buffer fluid. In this embodiment, the set of fifth and sixth heat exchangers are also is coupled to, in series with and is downstream of the fourth heat exchanger. As shown in FIG. 1W, the steam heat input for the gas separation plant de-ethanizer can be 0 MW because the alternative flow paths disclosed in this configuration may satisfy the entire heat load for the operation of the column. In an alternative embodiment, the steam heat input for the de-ethanizer column can be reduced because the alternative flow path disclosed in this configuration may partially satisfy the heat load for the operation of the column. Also as shown in FIG. 1W, the steam heat input for the C3/C4 splitter can be 0 MW because the alternative flow paths disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

The first portion of the combined heated buffer fluid exiting the fifth heat exchanger and the second portion of the combined heated buffer fluid exiting the sixth heat exchanger are re-combined and flowed to a collection header or the buffer fluid tank to repeat the waste heat recovery and reuse processes.

In some implementations, the heated buffer fluid can be flowed in series through the different plants. For example, the heated buffer fluid can be flowed first to the gas separation plant and then to the sour water stripper plant, and then flowed to a buffer fluid tank. The heated buffer fluid exiting the final exchanger(s) in the series can then be flowed to the buffer fluid tank. The buffer fluid from the buffer fluid tank can then be flowed to the different plants to restart the waste heat recovery and reuse cycle.

Such recovery and reuse of waste heat indirectly from both the diesel hydrotreating plant and the natural gas steam reforming hydrogen plant can result in decreasing or eliminating the heat energy to heat the sour water stripper plant or the gas separation plant or a combination of them such as by about 44 MW.

Configuration 6

Figure 1Y:
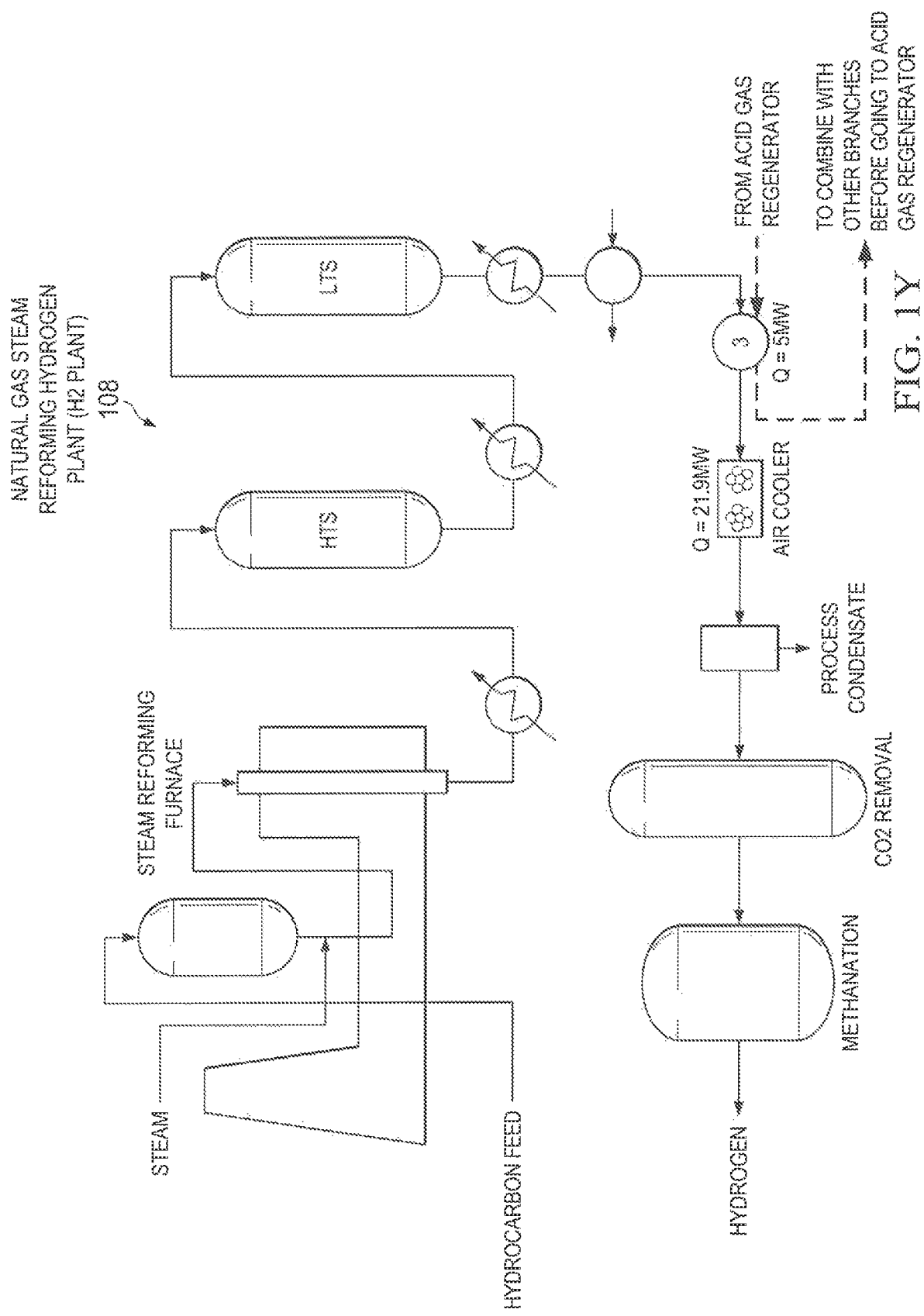
Figure 1Z:
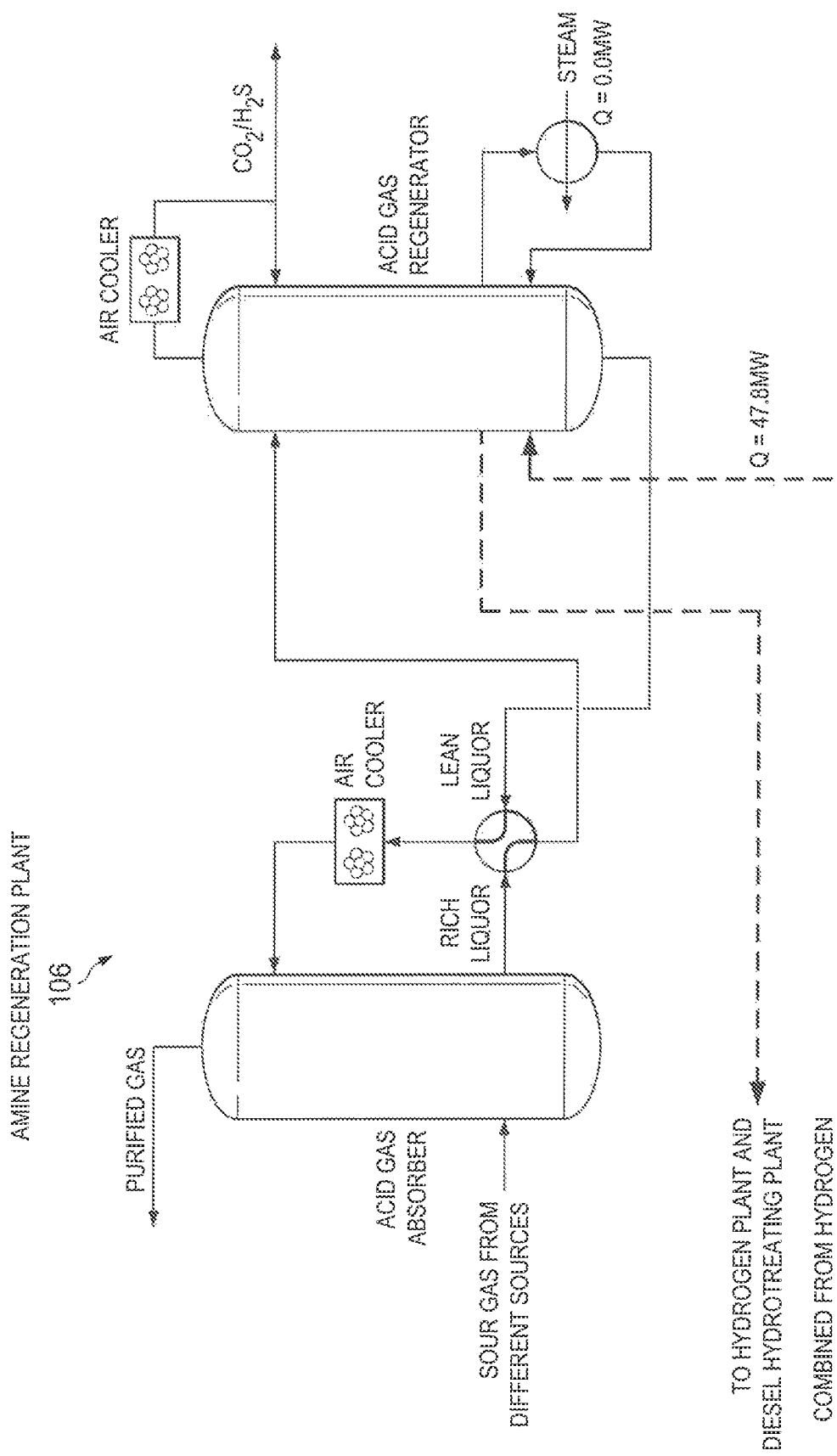

FIGS. 1X-1Z illustrate configurations and related scheme details for heating an acid gas regenerator bottom stream in an amine regeneration plant in the crude oil refining facility. In some implementations, a first stream in a first plant can be directly heated using multiple second streams in multiple second plants. In some implementations, the first plant is an amine regeneration plant; the first stream is the acid gas regenerator bottoms; the multiple second plants are the diesel hydrotreating plant and the natural gas steam reforming hydrogen plant; and the multiple second streams are the diesel stripper overheads, the diesel stripper bottoms and the low temperature shift (LTS) converter product streams.

The configurations illustrated in FIGS. 1X-1Z thermally integrate a diesel hydro-treating plant and a natural gas steam reforming hydrogen plant with an amine regeneration plant in a crude oil refining facility to reduce thermal energy consumption. A reduction in thermal energy consumption by about 48 MW can translate to about 12% of the heating utility consumption in the crude oil facility. As described later, in certain schemes, a process stream (for example, a diesel hydro-treating plant stream or other process streams) can be used to directly heat another process stream (for example, an acid gas regenerator bottom stream or other process stream). In certain configurations, heat exchange between process streams can be implemented using an intermediate buffer fluid, for example, water, oil, or other buffer fluid.

FIG. 1X shows a diesel hydro-treating plant 100 in a crude oil refining facility. The acid gas regenerator bottoms can be flowed into the plant as a single stream and split into multiple streams or it can be flowed into the plant as multiple streams. In some implementations, an acid gas regenerator bottom stream from an amine regeneration plant 106 is flowed to and is directly heated using a diesel stripper bottom product stream in a first heat exchanger (1, FIG. 1X). A second acid gas regenerator bottoms stream is directly heated using a diesel stripper overhead stream in a second heat exchanger (2, FIG. 1X). The first and the second heat exchangers are coupled in parallel with one another relative to the flow of acid gas regenerator bottoms. The thermal duties of the two heat exchangers can range between about 20 MW and 30 MW (for example, 23.2 MW) and 15 MW and 25 MW (for example, 19.6 MW), respectively. The transfer of heat directly to another process stream captures heat that would have otherwise been discharged to the environment. The diesel stripper overhead stream and the diesel stripper bottoms stream are returned to the diesel hydro-treating plant 100 for further processing.

FIG. 1Y shows a natural gas steam reforming hydrogen plant 108 in the crude oil refining facility. In some implementations, an acid gas regenerator bottoms stream from an amine regeneration plant 106 is flowed to and directly heated using a low temperature shift (LTS) converter product stream with a third heat exchanger (3, FIG. 1Y), which has a thermal duty that can range between about 1 MW and 10 MW (for example, 5 MW). The transfer of heat directly to another process stream captures heat that would have otherwise been discharged to the environment.

The heated first, second and third acid gas regenerator bottoms streams are combined and flowed to the amine regeneration plant 106. FIG. 1Z shows an amine regeneration plant 106. The first, second and third heat exchangers are coupled in parallel with one another relative to the flow of the acid gas regenerator bottoms. As shown, the steam heat input for acid gas regenerator can be 0 MW because the alternative flow paths disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

Such recovery and reuse of waste heat indirectly from both the diesel hydrotreating plant and the natural gas steam reforming hydrogen plant can result in decreasing or eliminating the heat energy to heat the amine regeneration plant such as by about 48 MW.

In summary, this disclosure describes configurations and related processing schemes of direct or indirect inter-plants heating systems (or both) synthesized for grassroots medium grade crude oil semi-conversion refineries to increase energy efficiency from specific portions of low grade waste heat sources. The disclosure also describes configurations and related processing schemes of mini-power plants synthesized for integrated medium grade crude oil semi-conversion refineries and aromatics complex for increasing energy efficiency from specific portions of low grade waste sources.

The economics of industrial production, the limitations of global energy supply, and the realities of environmental conservation are concerns for all industries. It is believed that the world's environment has been negatively affected by global warming caused, in part, by the release of GHG into the atmosphere. Implementations of the subject matter described here can alleviate some of these concerns, and, in some cases, prevent certain refineries, which are having difficulty in reducing their GHG emissions, from having to shut down. By implementing the techniques described here, specific plants in a refinery or a refinery, as a whole, can be made more efficient and less polluting by recovery and reusing from specific portions of low grade waste heat sources.

Thus, particular implementations of the subject matter have been described. Other implementations are within the scope of the following claims.

The invention claimed is:

1. A system implemented in a crude oil refining facility comprising a plurality of oil refining plants, each oil refining plant configured to perform at least one oil refining process, each oil refining plant comprising a plurality of interconnected oil refining sub-systems, wherein a plurality of streams at respective temperatures flow between the plurality of oil refining sub-systems, the system comprising:
a diesel hydro-treating plant stream from a diesel hydro-treating plant of the plurality of oil refining plants, the diesel hydro-treating plant stream comprising at least one of a diesel stripper bottom product stream or a diesel stripper overhead stream;
a stream from a first oil refining plant of the plurality of oil refining plants, the first oil refining plant being different from the diesel hydro-treating plant and comprising at least one of a sulfur recovery plant, an amine regeneration plant, a sour water stripper plant, or a gas separation plant through which a gas separation plant stream comprising at least one of C2 to C4 flows; and
a first heat exchanger configured to transfer heat from the diesel hydro-treating plant stream to the stream from the first oil refining plant.

2. The system of claim 1, wherein the first oil refining plant is the sulfur recovery plant, the stream is a sulfur recovery plant stream, and the system further comprises:
an oil refinery gas separation plant stream in an oil refinery gas separation plant of the plurality of oil refining plants; and
a second heat exchanger configured to heat the oil refinery gas separation plant stream using the heated sulfur recovery plant stream.

3. The system of claim 2, wherein the sulfur recovery plant stream is configured to be heated indirectly using the diesel hydro-treating plant stream.

4. The system of claim 3, further comprising:
a buffer fluid comprising a first buffer fluid stream and a second buffer fluid stream,
wherein the first heat exchanger is configured to heat the first buffer fluid stream using the diesel stripper bottom product stream;

a second heat exchanger configured to heat the second buffer fluid stream using the diesel stripper overhead stream; and
an amine regenerator in the sulfur recovery plant, the amine regenerator configured to receive the heated first buffer fluid stream and the heated second buffer fluid stream.

5. The system of claim 4, further comprising:
an amine regenerator bottom stream;
a third heat exchanger configured to heat the amine regenerator bottom stream using the heated first buffer fluid stream and the heated second buffer fluid stream; and
gas separation reboilers in the oil refinery gas separation plant, the gas separation reboilers configured to receive the heated first buffer fluid stream and the heated second buffer fluid stream.

6. The system of claim 5, further comprising:
a gas separation plant de-ethanizer stream;
a fourth heat exchanger configured to heat the gas separation plant de-ethanizer stream using the heated first buffer fluid stream and the heated second buffer fluid stream;
a C3/C4 splitter bottom stream; and
a fifth heat exchanger configured to heat the C3/C4 splitter bottom stream using the heated first buffer fluid stream and the heated second buffer fluid stream.

7. The system of claim 6, wherein the diesel hydro-treating plant is configured to receive the heated first buffer fluid stream and the second buffer fluid stream exiting the fourth heat exchanger and configured to receive the heated first buffer fluid stream and the heated second buffer fluid stream exiting the fifth heat exchanger.

8. The system of claim 4, wherein the buffer fluid comprises either water or oil.

9. The system of claim 6, wherein the first heat exchanger and the second heat exchanger are fluidically coupled to each other in parallel, wherein the third heat exchanger is fluidically coupled to a combination of the first heat exchanger and the second heat exchanger in series, wherein the fourth heat exchanger and the fifth heat exchanger are coupled to each other in parallel, and wherein the third heat exchanger is fluidically coupled to a combination of the fourth heat exchanger and the fifth heat exchanger in series.

10. The system of 1, wherein the stream from the first oil refining plant comprises an amine regenerator bottoms stream comprising a first stream and a second stream, wherein the first heat exchanger is configured to heat the first stream using the diesel stripper bottom product stream, and the system further comprises:
a second heat exchanger configured to heat the second stream using the diesel stripper overhead stream; and
an amine regenerator in the sulfur recovery plant, the amine regenerator configured to receive the heated first stream and the heated second stream.

11. The system of claim 10, wherein the first heat exchanger and the second heat exchanger are fluidically coupled to each other in parallel.

12. The system of claim 10, further comprising gas separation reboilers in the oil refinery gas separation plant, the gas separation reboilers configured to receive the diesel stripper bottom product stream from the first heat exchanger.

13. The system of claim 12, further comprising:
a gas separation plant de-ethanizer stream;
a third heat exchanger configured to heat the gas separation plant de-ethanizer stream using the diesel stripper bottom product stream;

a C3/C4 splitter bottom stream; and
a fourth heat exchanger configured to heat the C3/C4 splitter bottom stream using the diesel stripper bottom product stream.

14. The system of claim 13, wherein the diesel hydro-treating plant is configured to receive the diesel stripper bottom product stream exiting the third heat exchanger and the diesel stripper bottom product stream exiting the fourth heat exchanger.

15. The system of claim 13, wherein the third heat exchanger and the fourth heat exchanger are fluidically coupled to each other in parallel.

16. The system of claim 15, wherein the first heat exchanger is fluidically coupled in series with a combination of the third heat exchanger and the fourth heat exchanger.

17. The system of claim 1, wherein:
the first oil refining plant is an amine regeneration plant comprising an amine regeneration plant separation section amine regenerator bottom;
the stream is an acid gas regenerator bottoms stream from an acid gas regenerator in the amine regeneration plant;
the acid gas regenerator bottoms stream comprises a first stream and a second stream; and
the system further comprises:
a diesel stripper bottom product stream in the diesel hydro-treating plant, wherein the first heat exchanger is configured to heat the first stream using the diesel stripper bottom product stream;
a diesel stripper overhead stream in the diesel hydro-treating plant;
a second heat exchanger configured to heat the second stream using the diesel stripper overhead stream; and
an acid gas regenerator in the amine regeneration plant separation section, the acid gas regenerator configured to receive the heated first stream and the heated second stream.

18. The system of claim 17, wherein the first heat exchanger and the second heat exchanger are fluidically coupled to each other in parallel.

19. The system of claim 1, wherein the first oil refining plant is the gas separation plant, the stream is the gas separation plant stream, and the system further comprises:
a sour water stripper plant stream from a sour water stripper plant of the plurality of oil refining plants, the sour water stripper plant stream comprising a first stream and a second stream,
wherein the first heat exchanger configured to heat the first stream using the diesel stripper bottom product stream;
a second heat exchanger configured to heat the second stream using the diesel stripper overhead stream; and
a sour water stripper in the sour water stripper plant, the sour water stripper configured to receive the heated first stream and the heated second stream.

20. The system of claim 19, further comprising:
a C3/C4 splitter bottom stream;
a low temperature shift (LTS) converter product stream in a natural gas steam reforming hydrogen plant of the plurality of oil refining plants;
a third heat exchanger configured to heat the C3/C4 splitter bottom stream using the LTS converter product stream;
a gas separation plant de-ethanizer bottom stream; and
a fourth heat exchanger configured to heat the gas separation plant de-ethanizer bottom stream using the heated first stream and the second stream.

21. The system of claim 19, wherein the first heat exchanger and the second heat exchanger are fluidically coupled to each other in parallel, and wherein the third heat exchanger and the fourth heat exchanger are fluidically coupled to each other in parallel.

22. The system of claim 1, wherein the first oil refining plant is the amine regeneration plant, the stream is an acid gas regenerator bottoms stream, and the system further comprises:
a buffer fluid comprising a first stream and a second stream,
wherein the first heat exchanger is configured to heat the first stream using the diesel stripper bottom product stream;
a second heat exchanger configured to heat the second stream using the diesel stripper overhead stream; and
an acid gas recovery reboiler in the amine regeneration plant, the acid gas recovery reboiler configured to receive the heated first stream and the heated second stream.

23. The system of claim 22, wherein the buffer fluid further comprises a third stream, the plurality of oil refining plants comprises a natural gas steam reforming hydrogen plant, and the system further comprises:
a low temperature shift (LTS) converter product stream;
a third heat exchanger in the natural gas steam reforming hydrogen plant, the third heat exchanger configured to heat the third stream using the LTS converter product stream.

24. The system of claim 22, wherein the acid gas regenerator bottoms stream is configured to be heated by the heated first stream and the heated second stream from the diesel hydro-treating plant and the heated third stream from the LTS converter product natural gas steam reforming hydrogen plant.

25. The system of claim 24, wherein the first heat exchanger, the second heat exchanger and the third heat exchanger are fluidically coupled to each other in parallel.

26. The system of claim 1, wherein the first oil refining plant is the gas separation plant, the stream is the gas separation plant stream, and the system further comprises:
a sour water stripper plant stream from a sour water stripper plant in the crude oil refinery, the sour water stripper plant stream comprising a first stream and a second stream,
wherein the first heat exchanger is configured to heat the first stream using the diesel stripper bottom product stream;
a second heat exchanger configured to heat the second stream using the diesel stripper overhead stream; and
a sour water stripper in the sour water stripper plant, the sour water stripper configured to receive the heated first stream and the heated second stream.

27. The system of claim 26, further comprising:
a sour water stripper stream;
a low temperature shift (LTS) converter product stream in a natural gas steam reforming hydrogen plant of the plurality of oil refining plants;
a third heat exchanger configured to heat the sour water stripper stream using the LTS converter product stream.

28. The system of claim 27, wherein the gas separation plant is configured to receive the heated first stream, the heated second stream, and the heated sour water stripper stream, and the system further comprises:
a C3/C4 splitter in the gas separation plant;
a fourth heat exchanger configured to heat the C3/C4 splitter using the heated first stream, the heated second stream, and the heated sour water stripper stream;

a de-ethanizer reboiler in the gas separation plant; and
a fifth heat exchanger configured to heat the de-ethanizer reboiler using the heated first stream, the heated second stream, and the heated sour water stripper stream exiting the fourth heat exchanger.

29. The system of claim 28, further comprising:
a C3/C4 splitter in the gas separation plant;
a fourth heat exchanger in series with the first heat exchanger, the fourth heat exchanger configured to heat the C3/C4 splitter using the third stream cooled with sour water stripper stream in the first heat exchanger;
a de-ethanizer reboiler in the gas separation plant; and
a fifth heat exchanger configured to heat the de-ethanizer reboiler using the stream exiting the fourth heat exchanger in series with the first heat exchanger.

30. The system of claim 29, wherein the first heat exchanger, the second heat exchanger and the third heat exchanger are fluidically coupled to each other in parallel, wherein the third heat exchanger, and the fourth heat exchanger and the fifth heat exchanger are fluidically coupled to each other in series.

31. The system of claim 26, further comprising:
a buffer fluid comprising a first stream and a second stream,
wherein the first heat exchanger is configured to heat the first stream using the diesel stripper bottom product stream;
a second heat exchanger configured to heat the second stream using the diesel stripper overhead stream; and
a sour water stripper in the sour water stripper plant, the sour water stripper configured to receive the heated first stream and the heated second stream.

32. The system of claim 31, further comprising:
a low temperature shift (LTS) converter product stream in a natural gas steam reforming hydrogen plant of the plurality of oil refining plants; and
a third heat exchanger configured to heat the heated first stream and the heated second stream using the LTS converter product stream.

33. The system of claim 32, further comprising:
a C3/C4 splitter in the gas separation plant;
a fourth heat exchanger configured to heat the C3/C4 splitter using the heated first stream and the heated second stream;
a de-ethanizer reboiler in the gas separation plant; and
a fifth heat exchanger configured to heat the de-ethanizer reboiler using the heated first stream and the heated second stream exiting the fourth heat exchanger.

34. The system of claim 33, wherein the natural gas steam reforming hydrogen plant is configured to receive the heated first stream and the heated second stream exiting the fifth heat exchanger.

35. The system of claim 34, wherein the first heat exchanger, the second heat exchanger and the third heat exchanger are fluidically coupled to each other in parallel, wherein the fourth heat exchanger is coupled in series with a combination of the first heat exchanger, the second heat exchanger and the third heat exchanger.

36. The system of claim 1, wherein the first oil refining plant is the amine regeneration plant, the stream is an acid gas regenerator bottoms from an acid gas regenerator in the amine regeneration plant, the acid gas regenerator bottoms comprising a first stream and a second stream, wherein the first heat exchanger is configured to heat the first stream using the diesel stripper bottom product stream and the system further comprises
a second heat exchanger configured to heat the second stream using the diesel stripper overhead stream.

37. The system of claim 36, wherein the acid gas regenerator bottoms further comprises a third stream, the system further comprises a stream exiting a low temperature shift converter in a natural gas steam reforming hydrogen plant in the crude oil refinery, and the third stream is configured to be heated by the stream exiting the low temperature shift converter.

38. The system of claim 37, wherein the acid gas regenerator bottoms is configured to be heated by the heated first stream, the heated second stream, and the heated third stream.

39. The system of claim 38, wherein the first heat exchanger and the second heat exchanger are fluidically coupled to each other in parallel.

40. The system of claim 1, further comprising a flow control system.

* * * * *